(12) United States Patent
Gholap et al.

(10) Patent No.: US 7,979,212 B2
(45) Date of Patent: Jul. 12, 2011

(54) METHOD AND SYSTEM FOR MORPHOLOGY BASED MITOSIS IDENTIFICATION AND CLASSIFICATION OF DIGITAL IMAGES

(75) Inventors: Abhijeet S. Gholap, Cupertino, CA (US); Gauri A. Gholap, Cupertino, CA (US); Chiruvolu V. K. Rao, San Jose, CA (US); Sanford H. Barsky, Columbus, OH (US); Madhura Vipra, Prune (IN); Suhas Hanmantrao Patil, Prune (IN); Prithviraj Jadhav, San Jose, CA (US); Jayant Abhyankar, San Jose, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 837 days.

(21) Appl. No.: 11/048,541

(22) Filed: Jan. 31, 2005

(65) Prior Publication Data

US 2005/0266395 A1 Dec. 1, 2005

Related U.S. Application Data

(63) Continuation of application No. 10/938,314, filed on Sep. 10, 2004, and a continuation of application No. 10/966,071, filed on Oct. 15, 2004, now abandoned.

(60) Provisional application No. 60/540,767, filed on Jan. 31, 2004, provisional application No. 60/501,412, filed on Sep. 10, 2003, provisional application No. 60/515,582, filed on Oct. 30, 2003, provisional application No. 60/530,174, filed on Dec. 15, 2003.

(51) Int. Cl.
*G01N 33/48* (2006.01)
*G06K 9/00* (2006.01)

(52) U.S. Cl. ............ 702/19; 128/922; 382/133; 702/20; 703/11

(58) Field of Classification Search .................. None
See application file for complete search history.

(56) References Cited

U.S. PATENT DOCUMENTS

| | | | |
|---|---|---|---|
| 4,724,543 A | 2/1988 | Klevecz |
| 5,018,209 A | 5/1991 | Bacus |
| 5,526,258 A | 6/1996 | Bacus |
| 5,544,650 A | 8/1996 | Boon et al. |
| 5,546,323 A | 8/1996 | Bacus et al. |
| 6,009,342 A | 12/1999 | Brasch et al. |
| 6,151,405 A | 11/2000 | Douglass |
| 6,215,892 B1 | 4/2001 | Douglass |
| 6,330,349 B1 | 12/2001 | Hays |
| 6,365,362 B1 | 4/2002 | Terstappen |
| 6,404,916 B1 | 6/2002 | de la Torre-Bueno |
| 6,418,236 B1 | 7/2002 | Ellis |
| 6,445,817 B1 | 9/2002 | de la Torre-Bueno |
| 6,479,493 B1 | 11/2002 | Whitehead et al. |
| 6,518,554 B1 | 2/2003 | Zhang |
| 6,546,123 B1 | 4/2003 | McLaren |
| 6,553,135 B1 | 4/2003 | Douglass |
| 6,605,342 B1 | 8/2003 | Burghaus et al. |
| 6,631,203 B2 | 10/2003 | Ellis |
| 6,645,731 B2 | 11/2003 | Terstappen |
| 6,671,393 B2 | 12/2003 | Hays |
| 6,674,881 B2 | 1/2004 | Bacus |
| 6,674,884 B2 | 1/2004 | Bacus et al. |
| 6,674,896 B1 | 1/2004 | de la Torre-Bueno |
| 6,697,509 B2 | 2/2004 | de la Torre-Bueno |
| 6,711,283 B1 | 3/2004 | Soenksen |
| 6,718,053 B1 | 4/2004 | Ellis |
| 6,768,511 B1 | 7/2004 | Nakai |
| 6,775,402 B2 | 8/2004 | Bacus |
| 6,800,249 B2 | 10/2004 | de la Torre-Bueno |
| 6,900,426 B2 | 5/2005 | Zhang |
| 6,911,315 B2 | 6/2005 | Rimm |
| 6,914,613 B2 | 7/2005 | Marchand |
| 6,917,696 B2 | 7/2005 | Soenksen |
| 6,920,239 B2 | 7/2005 | Douglass |
| 2002/0009759 A1 | 1/2002 | Terstappen |
| 2002/0061542 A1 | 5/2002 | Rimm |
| 2002/0168657 A1 | 11/2002 | Chen |
| 2002/0172987 A1 | 11/2002 | Terstappen |
| 2003/0045451 A1 | 3/2003 | Bacus |
| 2003/0049701 A1 | 3/2003 | Muraca |
| 2003/0068626 A1 | 4/2003 | Wang |
| 2003/0073096 A1 | 4/2003 | Bao |
| 2003/0092047 A1 | 5/2003 | LaMorte et al. |

(Continued)

FOREIGN PATENT DOCUMENTS

EP 0283255 9/1988

(Continued)

OTHER PUBLICATIONS

Albert, et al. New method of nuclear grading of tissue sections by means of digital image analysis with prognostic significance for node-negative breast cancer patients. Cytometry. 1996; 24(2):140-50.

Comaniciu, et al. image-guided decision support system for pathology. Machine Vision and Applications. Springer, Verlag, DE. 1999; 11(4): 213-224.

(Continued)

*Primary Examiner* — Shubo Zhou

(57) ABSTRACT

A method and system for morphology based mitosis identification and classification of digital images. Luminance parameters such as intensity, etc. from a digital image of a biological sample (e.g., tissue cells) to which a chemical compound (e.g., a marker dye) has been applied are analyzed and corrected if necessary. Morphological parameters (e.g., size, elongation ratio, parallelism, boundary roughness, convex hull shape, etc.) from individual components within the biological sample are analyzed. A medical conclusion (e.g., type and count of mitotic cells) or a life science and biotechnology experiment conclusion is determined from the analyzed luminance and morphological parameters. The method and system may be used to develop applications for automatically obtaining a medical diagnosis (e.g., a carcinoma diagnosis).

21 Claims, 16 Drawing Sheets

U.S. PATENT DOCUMENTS

| | | |
|---|---|---|
| 2003/0096261 A1 | 5/2003 | Fruehauf |
| 2003/0129676 A1 | 7/2003 | Terstappen |
| 2003/0165263 A1 | 9/2003 | Hamer |
| 2003/0168577 A1 | 9/2003 | Zhang |
| 2003/0170703 A1 | 9/2003 | Piper |
| 2003/0215936 A1 | 11/2003 | Kallioniemi |
| 2003/0231791 A1 | 12/2003 | de la Torre-Bueno |
| 2004/0004614 A1 | 1/2004 | Bacus |
| 2004/0009098 A1 | 1/2004 | de la Torre-Bueno |
| 2004/0066960 A1 | 4/2004 | McLaren |
| 2004/0071327 A1 | 4/2004 | Ellis |
| 2004/0081345 A1 | 4/2004 | Douglass |
| 2004/0085443 A1 | 5/2004 | Kallioniemi |
| 2004/0115692 A1 | 6/2004 | Linder |
| 2004/0136582 A1 | 7/2004 | Bacus |
| 2004/0141637 A1 | 7/2004 | Bacus |
| 2004/0167806 A1 | 8/2004 | Eichhorn |
| 2004/0169883 A1 | 9/2004 | Eichhorn |
| 2004/0170325 A1 | 9/2004 | Eichhorn |
| 2004/0171036 A1 | 9/2004 | Wang |
| 2004/0171091 A1 | 9/2004 | Lesko |
| 2004/0176277 A1 | 9/2004 | Sowadski |
| 2004/0176372 A1 | 9/2004 | Suto |
| 2004/0180889 A1 | 9/2004 | Suto |
| 2004/0191854 A1 | 9/2004 | Lapen |
| 2004/1017031 | 9/2004 | Soenksen |
| 2004/0202357 A1 | 10/2004 | Perz |
| 2004/0210547 A1 | 10/2004 | Wentland |
| 2004/0214872 A1 | 10/2004 | Suto |
| 2004/0236773 A1 | 11/2004 | Bacus |
| 2004/0252875 A1 | 12/2004 | Crandall |
| 2004/0256538 A1 | 12/2004 | Olson |
| 2005/0003464 A1 | 1/2005 | Tibbe |
| 2005/0004024 A1 | 1/2005 | Tibbitts |
| 2005/0037406 A1 | 2/2005 | de la Torre-Bueno |
| 2005/0069900 A1 | 3/2005 | Lentrichia |
| 2005/0070020 A1 | 3/2005 | Klautky |
| 2005/0136493 A1 | 6/2005 | Rubin |
| 2005/0136509 A1 | 6/2005 | Gholap |
| 2005/0136549 A1 | 6/2005 | Gholap et al. |
| 2005/0181463 A1 | 8/2005 | Rao |
| 2006/0014238 A1 | 1/2006 | Gholap et al. |

FOREIGN PATENT DOCUMENTS

| | | |
|---|---|---|
| JP | 2000/224595 | 8/2000 |
| WO | WO 03/105675 | 12/2003 |

OTHER PUBLICATIONS

Drezet, et al. Automatic mitotic index estimation for the prognostication of breast cancer from histology images. IEE Colloquium Intelligent Methods in Healthcare and Medical Applications. Oct. 20, 1998. pp. 14-1.

Gao, et al. Computer-aided prostrate cancer diagnosis using image enhancement and JPEG 2000. Proceedings-SPIE the International Society for Optical Eng. International Society for Optical Engineering; Applications of Digital Image Processing XXVI. 2003; 5203;323-334.

Hatanaka, et al. Quantitative immunohistochemical evaluation of HER2/neu expression with HercepTestTM in breast carcinoma by image analysis. Pathol Int. 2001; 51(1):33-6.

Kate, et al. Method for counting mitoses by image processing in Feulgen stained breast cancer sections. Cytometry. 1993;14(3):241-50.

Krtolica, et al. Quantification of epithelial cells in coculture with fibroblasts by fluorescence image analysis. Cytometry. 2002; 49(2):73-82.

Madachy, et al. Image analysis for automatic classification of miotic cervical cells. Proceedings of the Annual International Conference of the IEEE Engineering in Medicine and Biology Society. Nov. 4, 1988. pp. 372-374.

Rodenacker, et al. A feature set for cytometry on digitized microscopic images. Anal Cell Pathol. 2003; 25(1):1-36.

Sunbland, et al. The use of image analysis and automation for measuring mitotic index in apical conifer rneristems. Journal of Experimental Botany. 1998; 49:1749-1756.

Van Der Laak, et al. Development and validation of a computerized cytomorphometric method to assess the maturation of vaginal epithelial cells. Cytometry. 1999; 35(3):196-202.

Weyn, et al. Automated breast tumor diagnosis and grading based on wavelet chromatin texture description. Cytometry. 1998; 33(1):32-40.

Gallart Biotech. Monoclonal Antibody Index. vol. 1: cancer. Available at: http://www.gallartinternet.com/mai. Accessed on Aug. 4, 2008.

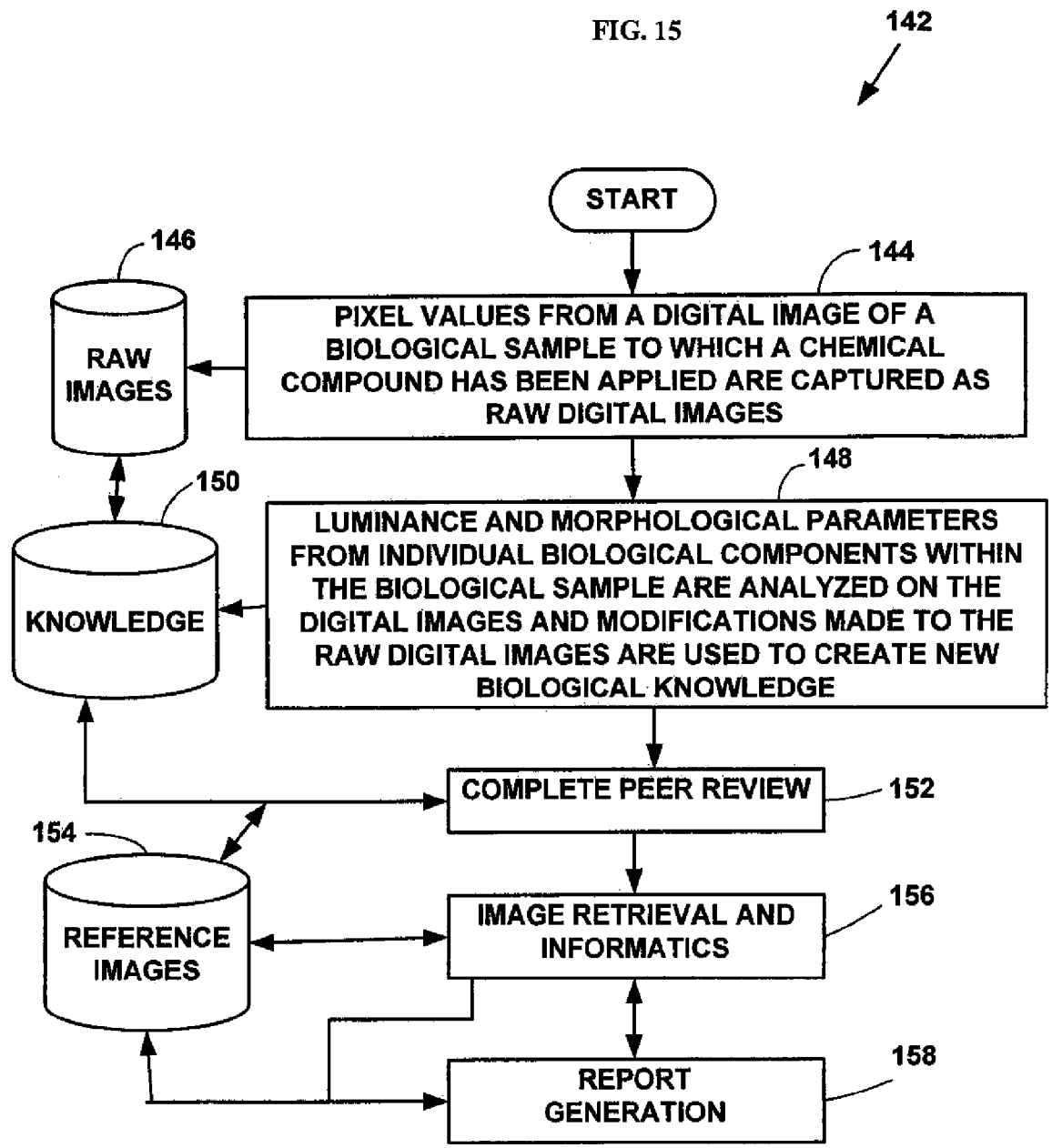

METHOD AND SYSTEM FOR MORPHOLOGY BASED MITOSIS IDENTIFICATION AND CLASSIFICATION OF DIGITAL IMAGES

CROSS REFERENCES TO RELATED APPLICATIONS

This application claims priority to U.S. Provisional Patent Application No. 60/540,767 filed Jan. 31, 2004, the contents of which are incorporated by reference. This application is a continuation-in-part application of U.S. patent application Ser. No. 10/938,314, filed Sep. 10, 2004, which claims priority to U.S. Provisional Patent Application No. 60/501,142, filed Sep. 10, 2003, and U.S. Provisional Patent Application No. 60/515,582, filed Oct. 30, 2003, and this application also claims priority to U.S. patent application Ser. No. 10/966,071, filed Oct. 15, 2004, which claims priority to U.S. Provisional Patent Application No. 60/530,714, filed Dec. 15, 2003, the contents of which are incorporated herein by reference in their entirety.

COPYRIGHT NOTICE

Pursuant to 37 C.F.R. 1.71(e), applicants note that a portion of this disclosure contains material that is subject to and for which is claimed copyright protection, such as, but not limited to, digital photographs, screen shots, user interfaces, or any other aspects of this submission for which copyright protection is or may be available in any jurisdiction. The copyright owner has no objection to the facsimile reproduction by anyone of the patent document or patent disclosure, as it appears in the Patent Office patent file or records. All other rights are reserved, and all other reproduction, distribution, creation of derivative works based on the contents, public display, and public performance of the application or any part thereof are prohibited by applicable copyright law.

FIELD OF THE INVENTION

This invention relates to digital image processing. More specifically, it relates to a method and system for morphology based mitosis identification and classification of digital images.

BACKGROUND OF THE INVENTION

In the field of medical diagnostics and research, pathology, drug discovery and clinical trials, detection, identification, quantification, and characterization of cells of interest, such as cancer cells, is an important aspect of diagnosis and research.

Pathologists use a number of properties in deciding the nature of a cell. Many of these properties do not have a rigid definition and many a times a pathologist provides a pathological decision based on many years of experience. A fundamental aspect of histopathology has been the recognition that the morphological appearance of a tumor can be correlated with a degree of malignancy. In many areas of histopathology, such as a diagnosis of breast carcinoma, does not give enough information for the referring medical clinician to make decisions about patient prognosis and treatment. Therefore manual and automated scoring and grading systems used by pathologists have been developed which provide additional information to medical clinicians. One of these automated scoring and grading systems includes considering mitotic activity of cells.

As is also known in the art, "Mitosis" is a process that facilitates the equal partitioning of replicated chromosomes into two identical groups. Mitosis is a last stage of cell cycle during which cells divide into two cells. In a typical animal cell, mitosis can be divided into four principal stages: (1) "Prophase:" where cell chromatin, diffuse in interphase, condenses into chromosomes. Each chromosome has duplicated and now consists of two sister chromatids. At the end of prophase, the nuclear envelope breaks down into vesicles; (2) "Metaphase:" where the chromosomes align at the equitorial plate and are held in place by microtubules attached to the mitotic spindle and to part of the centromere; (3) "Anaphase:" where the centromeres divide. Sister chromatids separate and move toward the corresponding poles; and (4) Telophase: where the daughter chromosomes arrive at the poles and the microtubules disappear. The condensed chromatin expands and the nuclear envelope reappears. The cytoplasm divides, the cell membrane pinches inward ultimately producing two daughter cells (e.g., "Cytokinesis").

Several studies have shown that the mitotic count is one of the most important variables in a grading system used for the prognosis of certain cancers including breast cancer. Histological grading has been one of the most important parameters in the determination of the prognosis of breast cancer. One of the important score of cancer grading systems is an evaluation of a Mitotic index of a tissue sample. As is known in the art a "Mitotic index" is an indication of a proliferative activity of a tumor.

Therefore mitotic scoring and grading systems have been developed which provide additional information. A Mitotic Activity Index ("MAI") is a useful and reproducible prognostic indicator for many cancers including invasive breast cancer. Traditionally, the MAI has been defined as the total number of mitoses counted in ten consecutive high-power fields (e.g., objective, ×40; numeric aperture, 0.75; field diameter, 450 microns), in an area subjectively determined to have most cellular activity at the periphery of the tumor.

There have been attempts to use mitosis prognostic indicator for many cancers. For example, a publication entitled "Mitotic frequency as a prognostic factor in breast cancer" by S. Biesterfeld, I. Noll, E. Noll, D. Wohltmann and A. Bocking, in Human Pathology 26: 47-52 (1995), describes a statistical analysis of prognostic significance of mitosis detection in breast cancer. The objective was to check mitotic grading of tumor malignancy in breast cancer contribute essential information both for the prospective outcome of the individual patient as well as for TNM staging. A series of 104 breast cancer patients were tested the prognostic validity and reproducibility of mitotic figure counting compared with TNM staging, Bloom and Richardson grading, DNA single cell cytometry, and morphometry. Depending on the number of mitotic figures, length of survival was significantly different. With a Cox stepwise regression model mitotic frequency counting was of higher prognostic significance than lymph node status, DNA ploidy, or mean nuclear area.

In another paper entitled "Comparison of the prognostic value of four methods to assess mitotic activity in 186 invasive breast cancer patients: classical and random mitotic activity assessments with correction for volume percentage of epithelium" by I. Jannink, P J van Diest, and J P Baak in Human Pathology 26: 1086-1092(1995) studies are done to check whether the prognostic value of mitotic activity could be improved by a random sampling procedure or correction for percentage of epithelium present. Proliferation markers and especially the Mitotic Activity Index (MAI) are strong and reproducible prognosticators in invasive breast cancer. For this purpose the prognostic value of four methods used to assess mitotic activity in invasive breast cancer was compared in 4-microns-thick hematoxylin-eosin (H&E)-stained sections of 186 primary invasive breast cancer patients. These were the MAI, the random MAI (rMAI), the Mitosis per Volume (M/V) Index, and the random M/V Index (rM/V Index). The rMAI was defined as the total number of mitotic figures counted in 10 random fields through the whole outlined tumor at ×400 magnification. All four methods checked had additional prognostic value to tumor size and lymph node status MAI, however, produced the best results, confirming importance of MAI in prognosis of a carcinoma.

Many pitfalls however, may occur in the determination of the mitotic count which is complex and involved. Mitotic counts differ depending upon the area of tumors analyzed. Margin with the proliferative area give the best results. Mitosis occurs through four successive stages, which are prophase, metaphase, anaphase and telophase.

A mitosis score is assessed in the peripheral areas of the neoplasm and not in the sclerotic central zone. The neoplasm is scanned at intermediate magnification to determine the area in which mitoses are most abundant (usually areas of poor tubule formation where cells are arranged in sheets or large nests). Only definite mitotic figures are counted with care to avoid non-mitotic nuclei including pyknotic nuclei in the count.

Grading of some tumors, particularly of the breast, has been done by microscopic examination. In grading breast tumors, pathologists have traditionally used the Scarff-Bloom-Richardson system (see, Le Doussal, V., et al., Cancer 64(9): 1914 (1989)). Although the S-B-R grading of tumors was an attempt at objective quantitation, microscopic tumor grading, by its nature, is subjective. Additionally, to grade tumors, the tumor or the cells from a tumor need to be removed. This requires surgical techniques. Because of the subjective nature of tumor grading, the same pathologist should grade all the tumors. In addition, the pathologist should be well-trained in the grading of tumors by the S-B-R system. Alternatively, two pathologists can be used and the results obtained by each compared for consistency (Robbins, P., et al., Human Pathology. 26(8): 873 (1995)).

Tumors can be graded histopathologically on many different bases. As mentioned above, for malignant breast tumors, grading systems such as S-B-R are preferred because they provide objective values of malignancy grade. The pathologist using the S-B-R system looks to three structural characteristics when grading tumors: (1) nuclear pleomorphism; (2) mitotic index; and (3) the ability of the tumor to form tubular, glandular or capillary formations, i.e., ductoglandular differentiation (see, Le Doussal, supra). Tumors are graded by each criterion separately with 1 being the most normal (differentiated) and 3 the most aberrant (undifferentiated). The scores of the three criteria are added for a final tumor grade. Therefore, the scores can range from 3-5 (well differentiated) to 6-7 (moderately differentiated) and 8-9 (poorly differentiated). Another method is the Nottingham modified criteria of Bloom and Richardson. See Bloom, H. J. G. and Richardson, W. W., Br. J. Cancer 9: 359-377 (1957).

This tumor-grading method was based on histological features of tubule formation, nuclear pleomorphism, and mitotic activity, and points were assigned for each category accordingly. The overall tumor grade was the sum total of scores between 3-9. Tumors with poorly differentiated phenotypes (8-9 points) are likely to have less or no tubular structures, irregular and large nuclei, and high mitotic counts. Tumors with moderately (6-7 points) or well differentiated (3-5 points) phenotypes may have definite tubule formation, moderate outlines of epithelial cell shapes and uniformity of nuclear chromatin, and low mitotic indexes. Mitotic activity is graded as follows as per the Nottingham grading system, how many mitotic figures (all four phases) does the pathologist see in 10 high power (400× magnification) fields. The point score cutoffs depend upon the size of the high power field of the microscope that is used. In general, <5 mitoses per 10 high power fields=1 point, 5-10 mitoses/10 high power fields=2 points, 10 mitoses/10 high power fields=3 points.

Although the Nottingham grading system uses a scoring system based on the number of mitoses per 10 HPF's, the Oncologic Standards Committee considers that a mitotic count per square millimeter is most accurate. Mitoses are only counted in the invasive component of the lesion. Using Clinical Onocological Standards, Mitoses are only counted in an invasive component in a lesion as is illustrated in Table 1.

TABLE 1

| Score 1: | <4 mitoses per square mm. |
|---|---|
| Score 2: | 4-7 mitoses per square mm. |
| Score 3: | >7 mitoses per square mm. |

Alternatively the number of mitoses in 10 high power fields (HPFs) is counted. Using an optical microscope with a 40× objective lens (i.e. ×400) and a field surface area of 0.152 $mm^2$, the scores are illustrated in Table 2.

TABLE 2

| Score 1: | 0-5 mitoses |
|---|---|
| Score 2: | 6-10 mitoses |
| Score 3: | >10 mitoses |

In practice, Contesso's method of scoring of mitoses is quicker and easier to perform especially on small biopsies (e.g., core biopsies). At least twenty high power fields of the same area as stated above are assessed and scored as is illustrated in Table 3.

TABLE 3

| Score 1: | No field contains more than 1 mitosis. |
|---|---|
| Score 2: | Two mitoses present in any one HPF. |
| Score 3: | Three or more mitoses present in any one HPF. |

Other studies have shown mitotic activity index has been shown to be important parameter in medical prognosis. A report by Lynch J, et al., (J Pathol. March 2002; 196(3): 275-9) has shown that use of the mitotic count (MC), which was assessed as part of the grading system, enabled patients to be stratified into "good" and "bad" prognostic groups. Another report by C. Patel et al., (Indian J. Pathol Microbiol. July 2002; 45(3): 247-54.) shows that MAI counted with strict criteria of Elston C W, emerged as one of the most significant prognostic parameter followed by overall grade in predicting Tumor free survival (TFS) for the patients.

Whichever is the system followed, accuracy of the detection of mitotic count is most essential. An overall grade of neoplasm is determined by adding individual score of the three separate parameters, tubules, nuclei and mitoses. The grading of the neoplasm has a very important role to play in the treatment and prognosis of the patient.

However, there are several problems associated using mitosis or a Mitosis index for diagnosing cancer. First, there is a difference in the mitotic counts depending upon the area of tumors analyzed by pathologists. Margins within a proliferative growth area of a tissue sample typically give the best results. However, many tissue samples are not analyzed in a proliferative growth area by pathologists.

Second, Mitosis occurs through four successive stages, which are pro-phase, metaphase, anaphase and telophase. A Mitosis score is typically assessed in peripheral areas of the neoplasm and not in a sclerotic central zone. Thus, the neoplasm is typically scanned at intermediate magnification with an optical microscope to determine an area in which mitoses are most abundant (e.g., usually areas of poor tubule formation where cells are arranged in sheets or large nests). Only definite mitotic figures are counted with care to avoid non-mitotic nuclei including pyknotic nuclei in the count.

It is observed that the seemingly simple task of mitotic cell counting becomes difficult because the counting has to be done for large number of sections. Benign and low grade cancers exhibit less than nine mitotic cells in a ten high power fields of view. Even experienced pathologist might miss genuine mitotic cells due to fatigue. Examination of tissue images typically has been performed manually by either a lab technician or a pathologist. In the manual method, a slide prepared with a biological sample is viewed at a low magnification under an optical microscope to visually locate candidate cells of interest. Those areas of the slide where cells of interest are located are then viewed at a higher magnification to count those objects as cells of interest, such as mitotic cells. In the last few years, slides with stained biological samples are photographed to create digital images from the slides. Digital images are typically obtained using an optical microscope and capturing a digital image of a magnified biological sample.

A digital image typically includes an array, usually a rectangular matrix, of pixels. Each "pixel" is one picture element and is a digital quantity that is a value that represents some property of the image at a location in the array corresponding to a particular location in the image. Typically, in continuous tone black and white images the pixel values represent a "gray scale" value.

Pixel values for a digital image typically conform to a specified range. For example, each array element may be one byte (i.e., eight bits). With one-byte pixels, pixel values range from zero to 255. In a gray scale image a 255 may represent absolute white and zero total black (or visa-versa).

Color images consist of three color planes, generally corresponding to red, green, and blue (RGB). For a particular pixel, there is one value for each of these color planes, (i.e., a value representing the red component, a value representing the green component, and a value representing the blue component). By varying the intensity of these three components, all colors in the color spectrum typically may be created.

However, many images do not have pixel values that make effective use of the full dynamic range of pixel values available on an output device. For example, in the eight-bit or byte case, a particular image may in its digital form only contain pixel values that fall somewhere in the middle of the gray scale range. Similarly, an eight-bit color image may also have RGB values that fall within a range some where in middle of the range available for the output device. The result in either case is that the output is relatively dull in appearance.

The visual appearance of an image can often be improved by remapping the pixel values to take advantage of the full range of possible outputs. That procedure is called "contrast enhancement." While many two-dimensional images can be viewed with the naked eye for simple analysis, many other two-dimensional images must be carefully examined and analyzed. One of the most commonly examined/analyzed two-dimensional images is acquired using a digital camera connected to an optical microscope.

One type of commonly examined two-dimensional digital images is digital images made from RGB values. Such digital images are commonly used to analyze biological samples including a determination of certain knowledge of medical conditions for humans and animals. For example, digital images are used to determine cell proliferate disorders such as cancers, etc. in humans and animals.

However, there are several problems associated using Mitosis or a Mitosis index for diagnosing cancer. First, there is a difference in the mitotic counts depending upon the area of tumors analyzed by pathologists. Margins within a proliferative growth area of a tissue sample typically give the best results. However, many tissue samples are not analyzed in a proliferative growth area by pathologists. Second, Mitosis occurs through four successive stages, which are pro-phase, metaphase, anaphase and telophase. A mitosis score is typically assessed in peripheral areas of the neoplasm and not in a sclerotic central zone. Thus, the neoplasm is typically scanned at intermediate magnification with an optical microscope to determine an area in which mitoses are most abundant (e.g., usually areas of poor tubule formation where cells are arranged in sheets or large nests). Only definite mitotic figures are counted with care to avoid non-mitotic nuclei including pyknotic nuclei in the count.

There are also several problems associated with using existing digital image analysis techniques for analyzing images for determining mitotic cell count. One problem is that existing digital image analysis uses fluorescent signals to identify mitotic activity. Fluorescent signals are counted to determine the existence of mitotic activity. Since these signals are very small, there is need to image specimen slides at a very high resolution. Once there are a large number of image sections to be processed together, issues like seamless composition of tiles becomes an issue. Further, one needs to prepare a separate slide and capture images through fluorescent microscope.

Another problem is that Haematoxylin and Eosin (H/E) stained tissue used for determining digital saliency can also be used for identification and classification of mitosis. However, using H/E stained tissue with a fluorescent signal based mitosis count typically requires stacking image planes in three dimensions to get a focused image. Otherwise, the small fluorescent signals far below the surface of the tissue will give weak, blurred ring of fluorescent signals. Manual method used is time consuming and prone to error including missing areas of the slide including mitotic cells.

There have been attempts to solve some of the problems associated with automating manual methods for counting mitotic cells. For example, in an article entitled, "Real-Time Image Analysis of Cells Undergoing Mitotic Catastrophe," by Michael Mackey and Fiorenza Ianzini of University of Iowa describe experiments to determine the fate of cells undergoing mitotic catastrophe following radiation exposure using the Large Scale Digital Cell Analysis System (LSDCAS) at Real-Time Cell Analysis Facility. LSDCAS is a computer-controlled microscope system that is capable of automatically generating digital movies of over 1000 separate microscope fields over a three-week interval following treatment.

IMSTAR S. A., a French-based, company designs, manufactures and markets automated digital imaging systems for Life Sciences Research and Clinical departments in Cytogenetics, Pathology, Cytology, Functional genomic, Drug Development and Validation. IMSTAR launched PATH-FINDER™ automated, and cost effective Image Cytometer, associated with a number of Application Software Analysis modules to facilitate and speed up research and diagnostics. This system provides detection of cell proliferation within breast cancer cells.

CompuCyte Corporation, of Cambridge, Mass. has a product for Cell Cycle and DNA Content Analysis. The total amount of DNA per cell is stoichiometrically determined to obtain cell cycle distributions. In addition, one of the morphometric features obtained for segmented nuclei, analysis, is directly correlated with condensation of chromatin in nuclei and can be used to differentiate interphase cells from mitotic cells.

U.S. Pat. No. 6,605,432, entitled "High-throughput methods for detecting DNA methylation," that issued to Tim Hui-Ming Huang teaches "a method of method of hybridization, differential methylation hybridization (DMH) for high throughput methylation analysis of multiple CpG island loci. DMH utilizes nucleic acid probes prepared from a cell sample to screen numerous CpG dinucleotide rich fragments affixed on a screening array. Positive hybridization signals indicate the presence of methylated sites. Methods of preparing the hybridization probes and screening array are also provided."

U.S. Pat. No. 6,009,342, entitled "Imaging method for the grading of tumors," that issued to Brasch, et al. teaches "the endothelial integrity of microvessels is disturbed in malignant tumors. MRIs are used to define tumor microvascular permeabilities and correlated the permeabilities with histologic grade in tumors. Using macromolecular MRI contrast medium, tumor microvascular permeability values were discovered to be significantly lower in benign tumors than in carcinomas. In addition, the microvascular permeability values demonstrated a strong correlation with the histologic grade of carcinomas as determined by the Scarff-Bloom-Richardson grading system."

In U.S. Pat. No. 4,724,543, entitled "Method and apparatus for automatic digital image analysis," that issued to Robert R. Klevecz, et al. teaches a "method and apparatus for digitally analyzing continuous visual images, particularly with reference to the detection of mammalian cell mitotic events is disclosed. The visual images are analyzed by first extracting high frequency picture components, threshold comparison of such components and probing for annular objects indicative of putative mitotic cells. The detection of annulae is performed by an algorithm for recognizing rings of differential radii and compensating for other variations. Thereafter, spatial and temporal relationships between such objects is stored and compared to determine whether cell division occurred."

In U.S. patent application No. 20030092047, entitled "Methods of cytodiagnostic staging of neoplasia and squamous cell carcinoma," published by Vickie J. LaMorte et al. describes "Methods of diagnosing whether an epithelial tissue is an abnormal tissue by determining an expression pattern for PML in the epithelial tissue; determining an expression pattern for nuclear bodies in the epithelial tissue; determining SUMO-1 colocalization and comparing the expression pattern for PML and the expression pattern for nuclear bodies with a control are disclosed. Also disclosed are methods for diagnosing whether a subject has mild dysplasia, moderate dysplasia, Type A severe dysplasia, Type B severe dysplasia, cervical squamous cell carcinoma, or poorly-differentiated cervical squamous cell carcinoma by determining an expression pattern for PML in an epithelial tissue sample from the subject; determining an expression pattern for nuclear bodies in the epithelial tissue; determining SUMO-1 colocalization; and determining whether the expression pattern for PML, the expression pattern for nuclear bodies, and the SUMO-1 colocalization of the epithelial tissue sample is consistent with expression patterns expected for mild dysplasia, moderate dysplasia, Type A severe dysplasia, Type B severe dysplasia, cervical squamous cell carcinoma, or poorly-differentiated cervical squamous cell carcinoma."

In U.S. patent application No. 20030049701, entitled "Oncology tissue microarrays" published by Patrick J. Muraca, discloses "the invention provides oncology tissue microarrays. In one aspect, the microarrays comprise a plurality of cell and/or tissue samples, each sample representing a different type of cancer. In another aspect of the invention, each sample represents a different stage of cancer. In still a further aspect of the invention, samples are ordered on the substrate of the microarray into groups according to common characteristics of the patients from whom the samples are obtained. By dividing tissue samples on the substrate into different groupings representing different tissue types, subtypes, histological lesions, and clinical subgroups, the microarrays according to the invention enable ultra-high-throughput molecular profiling."

However, these attempts still do not solve all of the problems associated with analyzing a digital image of stained tissue for identification and classification of mitosis for medical diagnosis and prognosis. Thus, it is desirable to provide an automated mitosis identification and classification image analysis system.

SUMMARY OF THE INVENTION

In accordance with preferred embodiments of the present invention, some of the problems associated with automated mitotic cell analysis systems are overcome. method and system for morphology based mitosis identification and classification of digital images is presented.

Luminance parameters such as intensity, etc. from a digital image of a biological sample (e.g., tissue cells) to which a chemical compound has been applied are analyzed. Mitotic cells present in the field of view are automatically identified and classified. The method and system may improve the prognosis and selection of appropriate therapy and prediction of therapeutic outcome based on mitotic cell identification and counting.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIG. 14 is a block diagram illustrating an example of convex hull part in a mitotic cell boundary;

FIG. 15 is a block diagram illustrating an exemplary flow of data in the automated digital image based mitosis detection and classification system;

DETAILED DESCRIPTION OF THE INVENTION

Exemplary Mitosis Identification and Classification System

Figure 1:
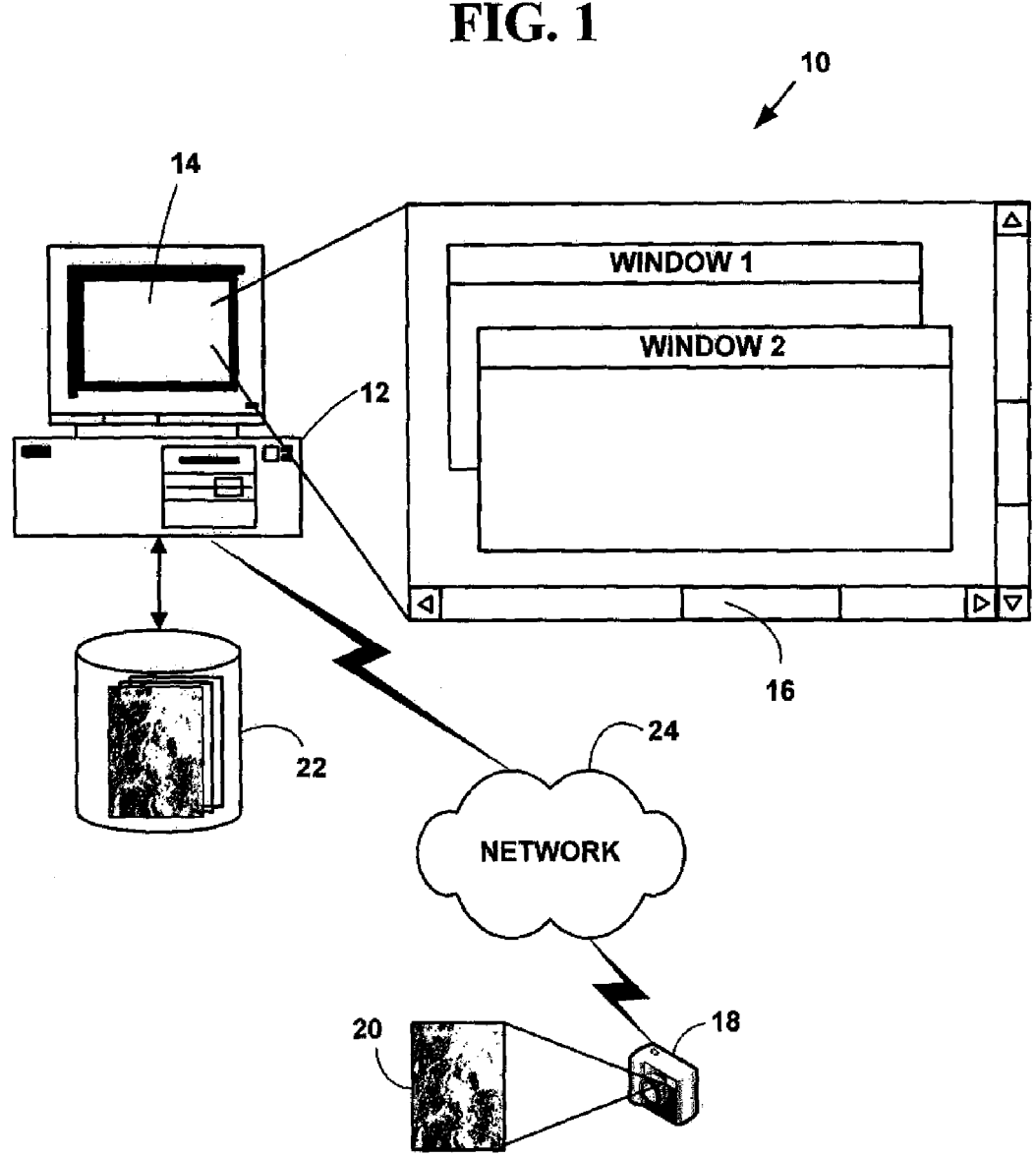
FIG. 1 is a block diagram illustrating an exemplary automated digital image based mitosis detection and classification system.

FIG. 1 is a block diagram illustrating an exemplary automated digital image based mitosis detection and classification system 10. The exemplary system 10 includes one or more computers 12 with a computer display 14 (one of which is illustrated). The computer display 14 presents a windowed graphical user interface ("GUI") 16 with multiple windows to a user. The system 10 may optionally include a microscope or other magnifying device (not illustrated in FIG. 1). The system 10 further includes a digital camera 18 (or analog camera) used to provide plural digital images 20 in various digital images or digital data formats. One or more databases 22 (one or which is illustrated) include biological sample information in various digital images or digital data formats. The one or more database 22 may also include raw and processed digital images and may further include knowledge databases created from automated analysis of the digital images 20, report databases and other types of databases as is explained below. The one or more databases 22 may be integral to a memory system on the computer 12 or in secondary storage such as a hard disk, floppy disk, optical disk, or other non-volatile mass storage devices. The computer 12 and the databases 22 may also be connected to an accessible via one or more communications networks 24.

The one or more computers 12 may be replaced with client terminals in communications with one or more servers, or with personal digital/data assistants (PDA), laptop computers, mobile computers, Internet appliances, one or two-way pagers, mobile phones, or other similar desktop, mobile or hand-held electronic devices.

The communications network 24 includes, but is not limited to, the Internet, an intranet, a wired Local Area Network (LAN), a wireless LAN (WiLAN), a Wide Area Network (WAN), a Metropolitan Area Network (MAN), Public Switched Telephone Network (PSTN) and other types of communications networks 24.

The communications network 24 may include one or more gateways, routers, or bridges. As is known in the art, a gateway connects computer networks using different network protocols and/or operating at different transmission capacities. A router receives transmitted messages and forwards them to their correct destinations over the most efficient available route. A bridge is a device that connects networks using the same communications protocols so that information can be passed from one network device to another.

The communications network 24 may include one or more servers and one or more web-sites accessible by users to send and receive information useable by the one or more computers 12. The one ore more servers, may also include one or more associated databases for storing electronic information.

The communications network 24 includes, but is not limited to, data networks using the Transmission Control Protocol (TCP), User Datagram Protocol (UDP), Internet Protocol (IP) and other data protocols.

As is know in the art, TCP provides a connection-oriented, end-to-end reliable protocol designed to fit into a layered hierarchy of protocols which support multi-network applications. TCP provides for reliable inter-process communication between pairs of processes in network devices attached to distinct but interconnected networks. For more information on TCP see Internet Engineering Task Force (ITEF) Request For Comments (RFC)-793, the contents of which are incorporated herein by reference.

As is know in the art, UDP provides a connectionless mode of communications with datagrams in an interconnected set of computer networks. UDP provides a transaction oriented datagram protocol, where delivery and duplicate packet protection are not guaranteed. For more information on UDP see IETF RFC-768, the contents of which incorporated herein by reference.

As is known in the art, IP is an addressing protocol designed to route traffic within a network or between networks. IP is described in IETF Request For Comments (RFC)-791, the contents of which are incorporated herein by reference. However, more fewer or other protocols can also be used on the communications network 19 and the present invention is not limited to TCP/UDP/IP.

The one or more database 22 include plural digital images 20 of biological samples taken with a camera such as a digital camera and stored in a variety of digital image formats including, bit-mapped, joint pictures expert group (JPEG), graphics interchange format (GIF), etc. However, the present invention is not limited to these digital image formats and other digital image or digital data formats can also be used to practice the invention.

The digital images 20 are typically obtained by magnifying the biological samples with a microscope or other magnifying device and capturing a digital image of the magnified biological sample (e.g., groupings of plural magnified cells, etc.).

An operating environment for the devices of the exemplary system 10 include a processing system with one or more high speed Central Processing Unit(s) ("CPU"), processors and one or more memories. In accordance with the practices of persons skilled in the art of computer programming, the present invention is described below with reference to acts and symbolic representations of operations or instructions that are performed by the processing system, unless indicated otherwise. Such acts and operations or instructions are referred to as being "computer-executed," "CPU-executed," or "processor-executed."

It will be appreciated that acts and symbolically represented operations or instructions include the manipulation of electrical signals by the CPU or processor. An electrical system represents data bits which cause a resulting transformation or reduction of the electrical signals or biological signals, and the maintenance of data bits at memory locations in a memory system to thereby reconfigure or otherwise alter the CPU's or processor's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic memory, and any other volatile (e.g., Random Access Memory ("RAM")) or non-volatile (e.g., Read-Only Memory ("ROM"), flash memory, etc.) mass storage system readable by the CPU. The computer readable medium includes cooperating or interconnected computer readable medium, which exist exclusively on the processing system or can be distributed among multiple interconnected processing systems that may be local or remote to the processing system.

The term "sample" includes cellular material derived from a biological organism. Such samples include but are not limited to hair, skin samples, tissue samples, cultured cells, cultured cell media, and biological fluids. The term "tissue" refers to a mass of connected cells (e.g., central nervous system (CNS) tissue, neural tissue, or eye tissue) derived from a human or other animal and includes the connecting material and the liquid material in association with the cells. The term "biological fluid" refers to liquid material derived from a human or other animal. Such biological fluids include, but are not limited to, blood, plasma, serum, serum derivatives, bile, phlegm, saliva, sweat, amniotic fluid, and cerebrospinal fluid (CSF), such as lumbar or ventricular CSF. The term "sample" also includes media containing isolated cells. One skilled in the art may determine the quantity of sample required to obtain a reaction by standard laboratory techniques. The optimal quantity of sample may be determined by serial dilution.

The term "biological component" include, but not limited to nucleus, cytoplasm, membrane, epithelium, nucleolus and stromal. The term "medical diagnosis" includes analysis and interpretation of the state of tissue material in a biological fluid. The interpretation includes classification of tissue sample as "benign tumor cell" or "malignant tumor cell". Interpretation also includes quantification of malignancy.

Mitosis

As is known in the art, Mitosis is a process of cell division, which results in the production of two daughter cells from a single parent cell. The daughter cells are identical to one another and to the original parent cell.

In a typical animal cell, mitosis can be divided into four principal stages illustrated in Table 4.

TABLE 4

| 1. | Prophase 28: The chromatin, diffuse in interphase, condenses into chromosomes. Each chromosome has duplicated and now consists of two sister chromatids. At the end of prophase, the nuclear envelope breaks down into vesicles. |
| 2. | Metaphase 30: The chromosomes align at the equitorial plate and are held in place by microtubules attached to the mitotic spindle and to part of the centromere. |
| 3. | Anaphase 32: The centromeres divide. Sister chromatids separate and move toward the corresponding poles. |
| 4. | Telophase 34: Daughter chromosomes arrive at the poles and the microtubules disappear. The condensed chromatin expands and the nuclear envelope reappears. The cytoplasm divides, the cell membrane pinches inward ultimately producing two daughter cells (phase: Cytokinesis). |

Digital Images

A digital image 20 typically includes an array, usually a rectangular matrix, of pixels. Each "pixel" is one picture element and is a digital quantity that is a value that represents some property of the image at a location in the array corresponding to a particular location in the image. Typically, in continuous tone black and white images the pixel values represent a gray scale value.

Pixel values for a digital image 20 typically conform to a specified range. For example, each array element may be one byte (i.e., eight bits). With one-byte pixels, pixel values range from zero to 255. In a gray scale image a 255 may represent absolute white and zero total black (or visa-versa).

Color images consist of three color planes, generally corresponding to red, green, and blue (RGB). For a particular pixel, there is one value for each of these color planes, (i.e., a value representing the red component, a value representing the green component, and a value representing the blue component). By varying the intensity of these three components, all colors in the color spectrum typically may be created.

However, many images do not have pixel values that make effective use of the full dynamic range of pixel values available on an output device. For example, in the eight-bit or byte case, a particular image may in its digital form only contain pixel values ranging from 100 to 150 (i.e., the pixels fall somewhere in the middle of the gray scale). Similarly, an eight-bit color image may also have RGB values that fall within a range somewhere in middle of the range available for the output device. The result in either case is that the output is relatively dull in appearance.

The visual appearance of an image can often be improved by remapping the pixel values to take advantage of the full range of possible outputs. That procedure is called "contrast enhancement." While many two-dimensional images can be viewed with the naked eye for simple analysis, many other two-dimensional images must be carefully examined and analyzed. One of the most commonly examined/analyzed two-dimensional images is acquired using a digital camera connected to an optical microscope.

One type of commonly examined two-dimensional digital images 20 are digital images made from biological samples including cells, tissue samples, etc. Such digital images are commonly used to analyze biological samples including a determination of certain know medical conditions for humans and animals. For example, digital images are used to determine cell proliferate disorders such as cancers, etc. in humans and animals.

Digital images 20 captured through optical microscopes represent the images seen by a human eye through the microscope. However, a pathologist can easily identify and distinguish between various phases of mitotic cells and non-mitotic cells, even though there are variations in staining, variations in illumination across a slide or the presence of a mask or an artifact. This is because of experience and knowledge of the domain of the pathologist.

The criteria for Mitosis identifications used by pathologist are illustrated in Table 4. However, more fewer or other mitotic activity can also be used to practice the invention and the present invention is not limited to the Mitosis identifications illustrated in Table 5. The present invention automates the identifications illustrated in Table 5.

TABLE 5

| 1. | A Mitotic nucleus is darker than the other nuclei & background. |
| 2. | A Mitotic nucleus is comparatively bigger in size. |
| 3. | A Mitotic nucleus has sharp edge angles at the boundary |

Exemplary Automated Biological Sample Analysis Method

Figure 2:
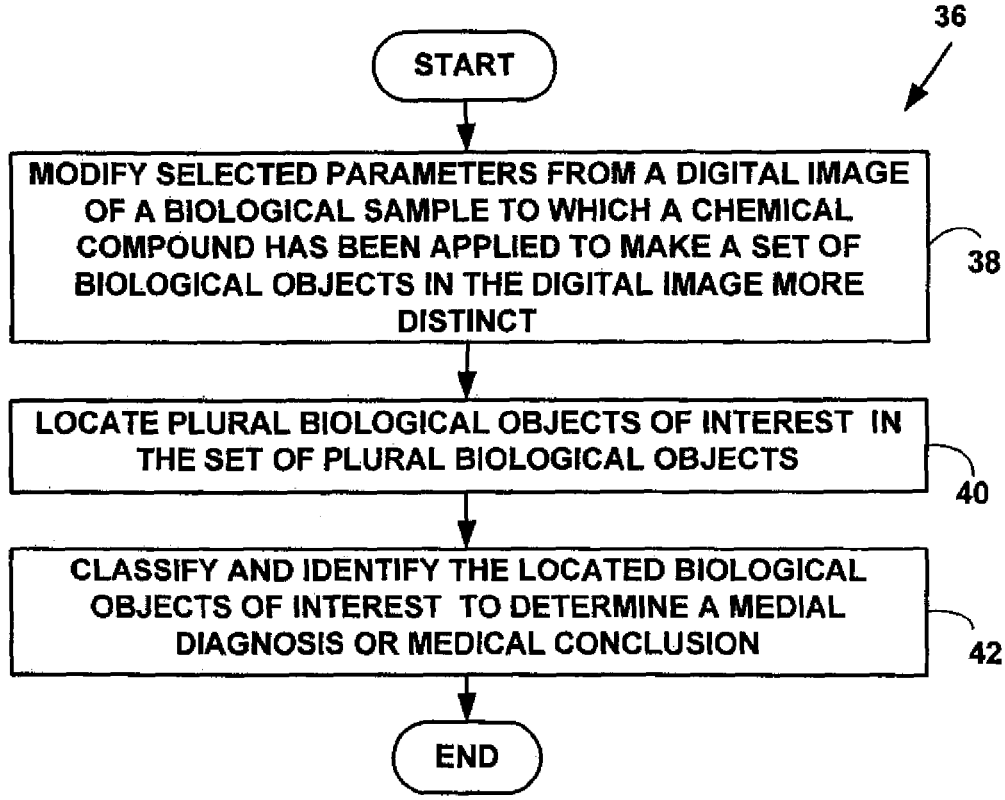
FIG. 2 is a flow diagram illustrating an automated method for automated biological sample analysis.

FIG. 2 is a flow diagram illustrating a Method 36 for automated biological sample analysis. At Step 38, pre-determined parameters from a digital image of a biological sample to which a chemical compound has been applied are modified to make a set of plural biological objects in the digital image more distinct. At Step 40, plural biological objects of interest are located in the set of plural biological objects. At Step 42, the located biological objects of interest are identified and classified to determine a medical diagnosis or medical conclusion.

Method 36 is illustrated with an exemplary embodiment. However, the present invention is not limited to such an embodiment and other embodiments can also be used to practice the invention.

In such an exemplary embodiment at Step 38, color parameters from a digital image 20 of a tissue sample including plural cells to which a staining dye has been applied are modified to create a set of plural cell objects in the digital image more distinct. The modifications include, but are limited to, contrast modification and correcting color components. A cell object as used herein includes a cell and its various cell components (e.g., membrane, nuclei, chromosomes, etc.).

In one embodiment of the invention, Step 38 is completed as a pre-processing method. However, the invention is not limited to such an embodiment and other embodiments can also be used to practice the invention.

Pre-processing methods reduce the effect of variations in staining intensity, effect of colored mask and other anamolies. Pre-processing methods typically have two distinct steps (1) Contrast modification of an input digital image based on image statistics; (2) Correcting color components of each pixel.

With respect to contrast modification, "contrast" in a digital image is referred to the difference in color values between any two given pixels. Color values at a given pixel are independently calculated from Red, Green and Blue components of the given color image. Contrast modification includes determining an active range of intensities in each of the colors. A histogram of all color planes (e.g., red, green and blue) of the digital image 20 are calculated. The calculated histograms are used to compute a minimum intensity such that, starting from lowest intensity, cumulative pixels up to minimum intensity is equal to about two percent of total pixels in the digital image. An active range intensity range of pixels in the digital image 20 is mapped to a range (zero, 255). All pixels with value less than minimum intensity are also set to zero.

An image is of high contrast if each color level ranges from minimum (zero) to maximum (255). In the case of low contrast images, this range could be as small as 50, for example from 100 to 150. If the contrast is high, the pixels belonging to a mitotic cell that appears dark, the cytoplasm appears moderately dark and the vacuoles will be brightest. Color correction is required for low contrast images and images with a color mask. Color corrections are made such that dark pixels become even darker and brighter pixels should maintain the same level of difference at least.

Effects of a color mask are also reduced or neutralized in digital images 20 with some color background. Color mask parameters are calculated from the calculated color planes using peak frequencies in respective calculated histograms. Ratios of the peak values in one or more color planes are used to correct pixels in the digital image 20.

Returning to FIG. 2 at Step 40, plural mitotic cells are located as objects of interest in a set of plural cells in a tissue sample in a digital image. In any given tissue sample image, there could be several hundred cells. These cells could be normal epithelial cells, stained epithelial cells, stromal cells or mitotic cells in any one of the mitotic phases 28, 30, 32, 34. Mitotic cells are located as objects of interest and non-mitotic cells are eliminated from further processing.

Returning to FIG. 2 at Step 42, the located mitotic cells are classified to determine a medical diagnosis or medical conclusion. For example a medical diagnosis may include a diagnosis of N-stage breast cancer. In one embodiment, the Nottingham grading system or counting a number of mitoses in ten high power fields (HPFS) is used to classify the mitotic cells. However, the present invention is not limited to such an embodiment and other classification system can be used to practice the invention.

Figure 3:
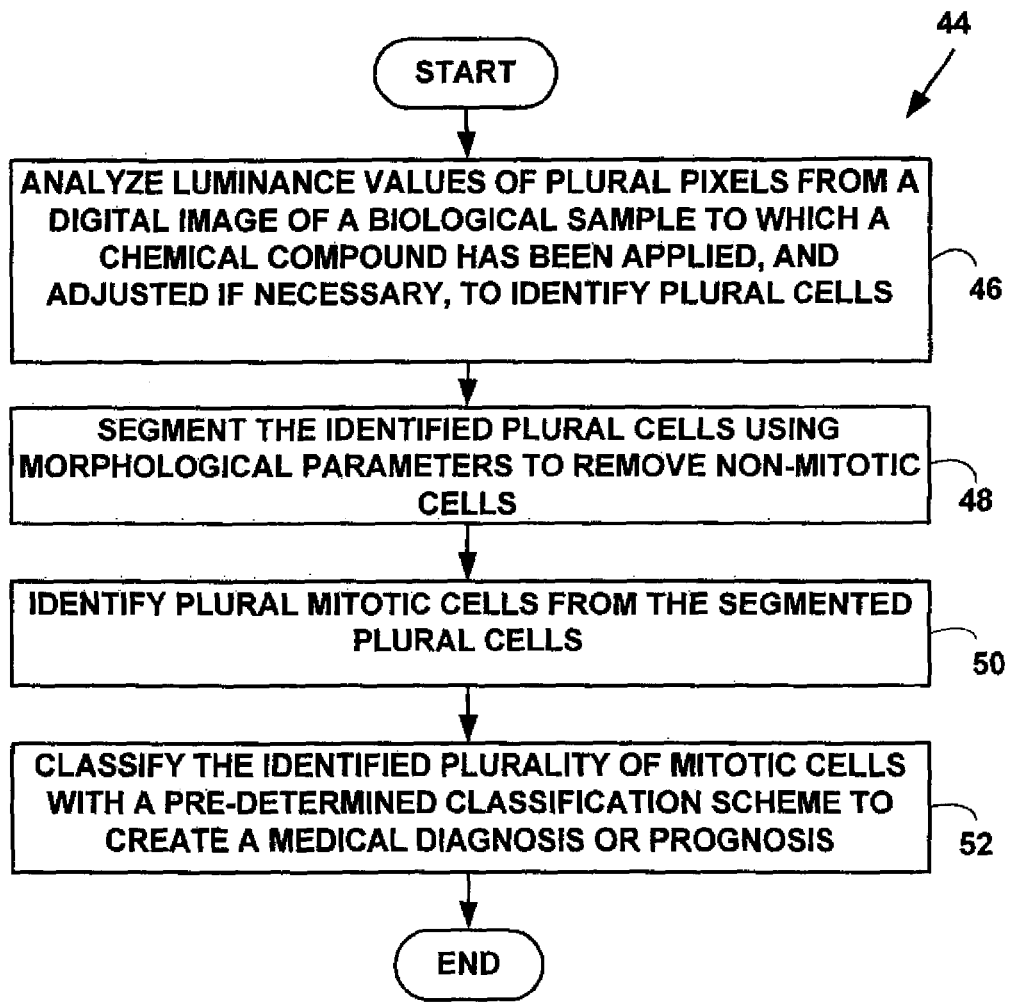
FIG. 3 is a block diagram illustrating an automated method for mitosis analysis.

FIG. 3 is a block diagram illustrating an automated Method 44 for mitosis analysis. At step 46, luminance values of plural pixels from a digital image of a biological sample to which a chemical compound has been applied are analyzed and adjusted if necessary, to identify plural cells. At step 48, the identified plural cells are segmented using morphological parameters to remove non-mitotic cells. At step 50, plural mitotic cells are identified from the segmented plural cells. At Step 52, the plural mitotic cells are classified using a pre-determined classification scheme to create a medical diagnosis or prognosis.

Method 44 may be specifically used by pathologists and other medical personnel to automatically analyze a tissue sample for mitotic cells and make a medical diagnosis or prognosis. However, the present invention is not limited to such an application and Method 44 may also be used for other purposes.

Method 44 may also be used for automatically determining diagnostic saliency of digital images for mitotic cells. This method can be used for automatically determining diagnostic saliency of digital images for mitotic cells and includes using one or more filters for evaluating digital images 20. Each filter is designed to identify a specific type of morphological parameter of a mitotic cell.

Methods 44 may also be used for automatically quantitatively analyzing biological samples. This method is use for automatically quantitatively analyzing relevant properties of the digital images, and creating interpretive data, images and reports resulting from such analysis.

Method 44 further include Step 53 (not illustrated in FIG. 3) to create one or more reports related to the medical diagnosis or prognosis created and present digital image 20 and the one or more types of reports generated for the medical diagnosis or prognosis on the GUI 14.

Digital images 20 captured through optical microscopes resemble a view a human pathologist gets through optical system of a microscope. However, a human pathologist based on his/her experience is in a position to easily distinguish between nuclei, cytoplasm, red blood cells, membranous pattern and fibrin, even-though there are variations in staining, variations in illumination across slide. A human pathologist has experience and knowledge of the domain of pathological analysis of tissue cells to distinguish between the various cellular components.

In one embodiment of the invention, Method 44 achieves the same and in most instances better results than those completed by a human pathologist, but in an automated manner (See, e.g., Table 9). However, the present invention is not limited this method and other methods can be used to practice the invention.

Method 44 is illustrated with one exemplary embodiment. However, the present invention is not limited to such an embodiment and other embodiments can also be used to practice the invention.

In such an exemplary embodiment at Step 46, luminance parameters such as intensity, etc. from a digital image 20 of a biological sample (e.g., tissue cells) to which a chemical compound (e.g., a marker dye) has been applied are analyzed and corrected if necessary to identify plural cells in the digital image.

In one embodiment, Step 46 includes a pre-processing method illustrated with Method 54. However, the present invention is not limited to such an embodiment and other methods can be used at Step 46 to practice the invention.

Figure 4:
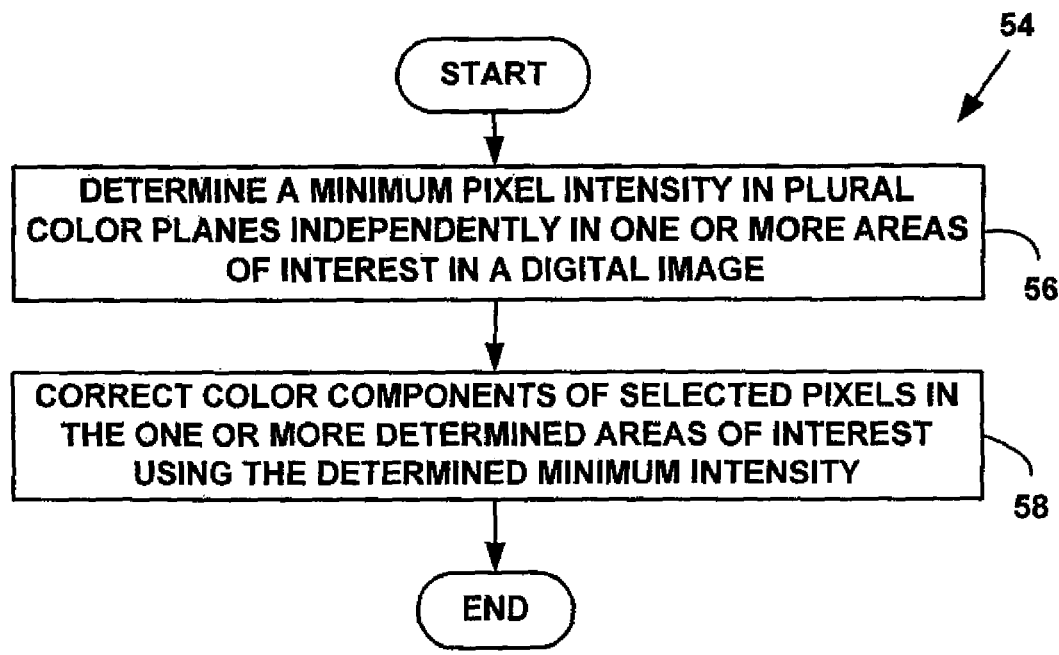
FIG. 4 is a flow diagram illustrating method for pre-processing digital images to identify mitotic cells.

FIG. 4 is a flow diagram illustrating Method 54 for pre-processing digital images to identify mitotic cells. At Step 56, a minimum pixel intensity is determined in plural color planes independently in one or more areas of interest in a digital image. At Step 58, color components of selected pixels in the one or more determined areas of interest (e.g., those including cells) are corrected using the determined minimum intensity. Method 54 is illustrated with one exemplary embodiment. However, the present invention is not limited to such an embodiment and other embodiments can also be used to practice the invention.

In such an exemplary embodiment, the pre-processing Method 54 includes, but is not limited to, at least two distinct steps: (1) Determining a minimum pixel intensity of a digital image based on digital image statistics at Step 56; and (2) correcting color components of selected pixels in the one or more determined areas of interest using the determined minimum intensity at Step 58. However, the present invention is not limited to these steps and more, fewer or other steps can also be used to practice the invention.

As was discussed above, "contrast" in a digital image is referred to a difference in luminosity level between any two given pixels. Contrast could be in the same color plane or across color planes. In the current invention Red, Green and Blue color planes are considered. In the prior art, other color models like Hue Saturation and Intensity (HSI) are used. However, pathologists use color information extensively. Further, the term Hue is interpreted by pathologists and image processing people differently. Therefore in the current invention, a RGB luminance model is used. In another embodiment, HSI are used. However, the present invention is not limited to these embodiments and other embodiments can also be used to practice the invention.

A digital image is considered "high contrast" if its luminosity levels range from a minimum value (e.g., zero) to a maximum value (e.g., 255). In the case of low contrast images, this range could be as small as zero to 50, for example, or range from 100 to 150.

In the case of high contrast images, the pixels belonging to cell nuclei and mitotic cells look dark and have a low luminosity, cytoplasm looks moderately dark has a moderate luminosity and vacuoles look bright and typically will be of a highest luminosity. Contrast modification helps improve low contrast images to aid automated analysis. Modification is used such that dark pixels become even darker and brighter pixels maintain at least a same level of initial brightness. Determining a minimum intensity in each color plane independently results in contrast enhancement in the active range of pixels in a digital image 20.

Figure 5:
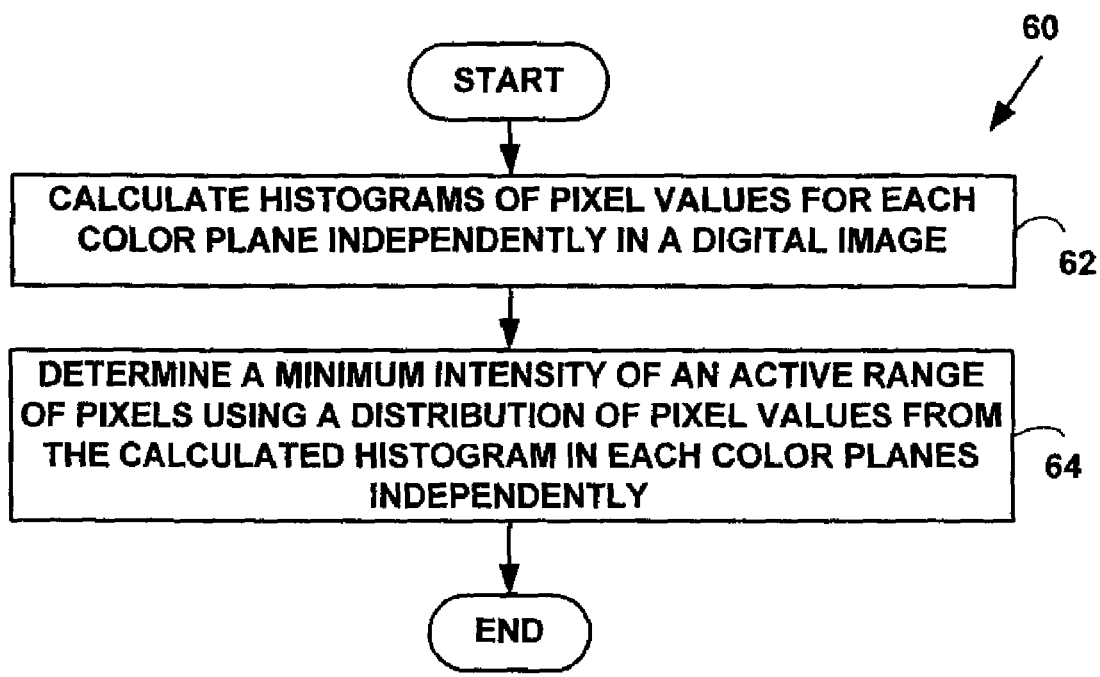
FIG. 5 is a flow diagram illustrating an exemplary method for determining a minimum intensity of plural pixels in a digital image to identify mitotic cells.

FIG. 5 is a flow diagram illustrating an exemplary Method 60 for determining a minimum intensity of plural pixels in a digital image to identify mitotic cells. At Step 62, histograms of pixel values are calculated for each color plane independently in a digital image. At Step 64, a minimum intensity of an active range of pixels is determined using a distribution of pixel values from the calculated histogram in each of the color planes independently.

Method 60 is illustrated with one exemplary embodiment. However, the present invention is not limited to such an embodiment and other embodiments can also be used to practice the invention.

In such an exemplary embodiment at Step 62, starting with a zero level, cumulative frequencies of pixel values in each of red, green and blue planes are calculated independently for the digital image 20.

Step 64, a threshold value is used for independently determining a minimum intensity in each color plane using the calculated cumulative frequencies. In one embodiment, the threshold value is two percent However, the present invention is not limited to this threshold value and other threshold values may be use to practice the invention.

Returning to FIG. 4 at Step 58, pixel values in each color plane are mapped such that pixel values in a first range {minimum intensity to maximum intensity} are mapped to a second range {zero to maximum intensity} to correct the color components and contrast enhance the digital image.

Contrast enhancement or difference between pixels level is increased by setting all pixels below minimum intensity level to zero, keeping and keeping maximum intensity in each color plane the same.

Figure 6:
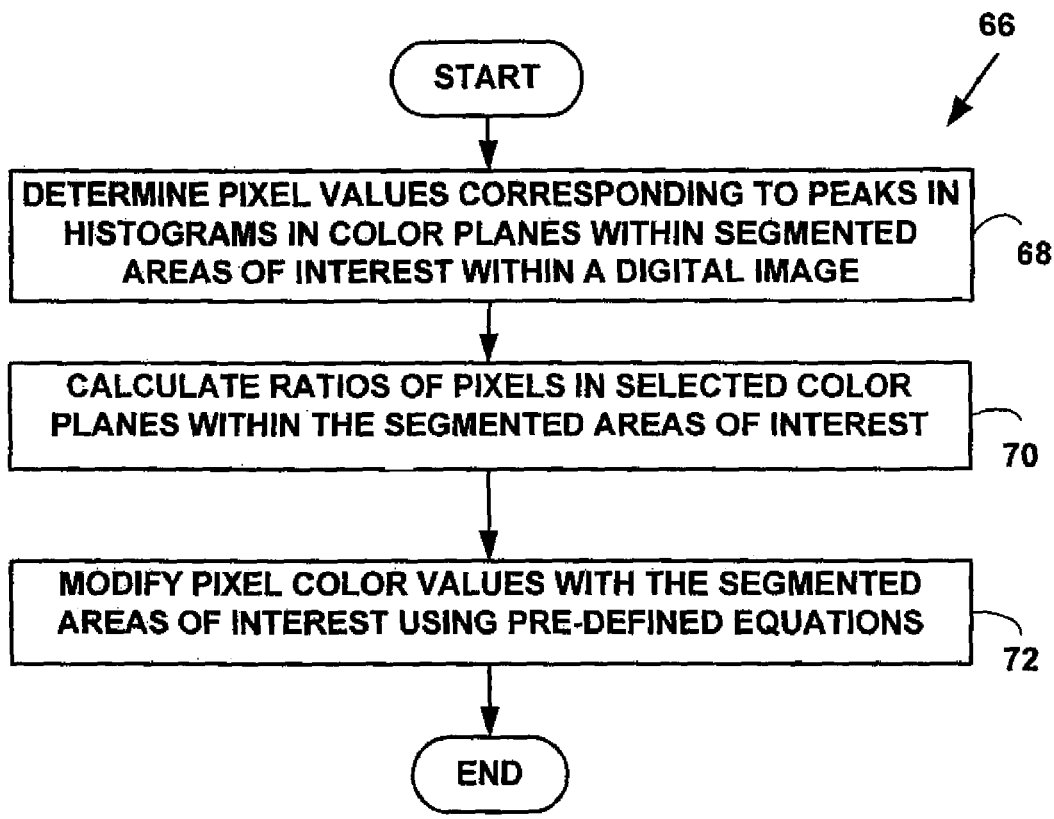
FIG. 6 is a flow diagram illustrating a method for contrast enhancement of a digital image to identify mitotic cells.

FIG. 6 is a flow diagram illustrating a Method 66 for contrast enhancement of a digital image to identify mitotic cells. At Step 68, pixel values corresponding to peaks in histograms in color planes within segmented areas of interest within a digital image are determined. At Step 70, ratios of pixels are calculated in selected color planes within the segmented areas of interest. The color planes used are determined by the chemical compound (e.g., staining such as H/E staining) applied to the biological tissue sample. At Step 72, pixel color values are modified with the segmented areas of interest using pre-defined equations.

Method 66 is illustrated with one exemplary embodiment. However, the present invention is not limited to such an embodiment and other embodiments can also be used to practice the invention.

In such an exemplary embodiment at Step 68, color mask parameters are calculated from the red, green and blue color planes using peak frequencies in respective histograms for the color planes.

At Step 70, ratios of peak frequency values are calculated in the appropriate color planes. The color planes used are determined by the chemical compound applied to the biological tissue sample.

Figure 7:
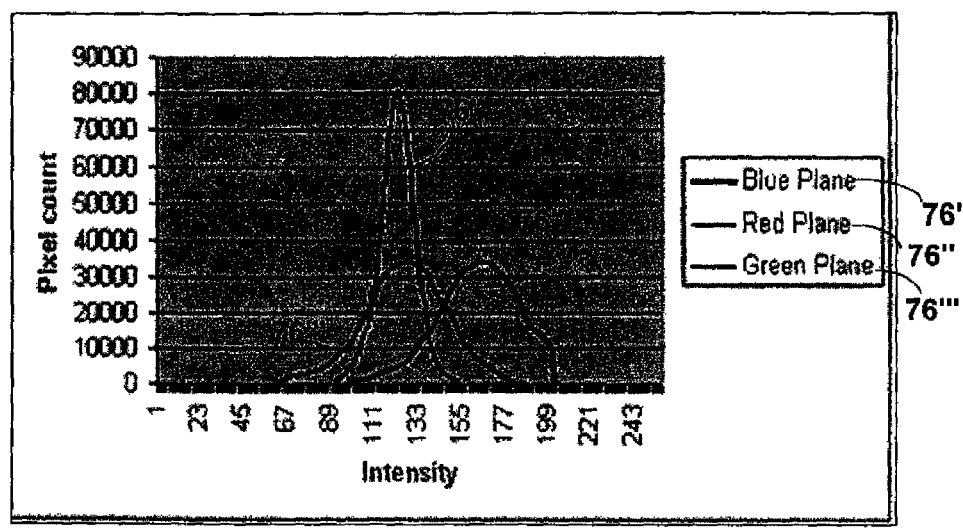
FIG. 7 is a block diagram with a histogram of blue, red and green color plane intensity values calculated from an original digital image.

FIG. 7 is a block diagram with a histogram 76 of blue 76', red 76" and 76'" color plane intensity values calculated from the original digital image 74.

In one embodiment, H/E staining is used so the red and blue color planes are used to calculate ratios at Step 70. For example, it is known that segmented objects in areas of interest, such as mitotic cells, nuclei are blue in color when stained with H/E staining and other stains. If a biological tissue sample was treated with other than H/E staining, then nuclei or other cell components may appear as a different color other than blue and thus other color planes would be used at Step 70.

This ratio calculation is based on chemical compound (e.g., a stain such as H/E stain) that has been applied to the biological sample. However, the invention is not limited to this embodiment and other ratios in other color planes can also be used to practice the invention. Based on the stain being used Equations (3) and (4) are used to compute the ratios of color plane histogram peaks.

$$X_f = \text{first color plane peak/second color plane peak} \quad (3)$$

$$Y_f = \text{second color plane peak/first color plane peak} \quad (4)$$

In one embodiment, the fist color plane is the red color plane and the second color plane is the blue color plane. The red peak and blue peak are respective color component values that have peak frequency as is illustrated in the histogram 76. If the image is predominantly blue colored, then a blue peak will be much larger than a red peak. If the image is predominantly red in color, then red peak will be larger than the blue peak. Histogram 76 illustrates a blue peak 76' much larger than a red peak 76". Equations (5) and (6) illustrate calculating ratios for am image that is primarily blue in color.

$$B_f = \text{Blue color plane peak/Red color plane peak} \quad (5)$$

$$R_f = \text{Red color plane peak/Blue color plane peak} \quad (6)$$

At Step 72, corrections to pixels color components are completed using histogram peaks and ratios. Equations (7), (8), and (9) are used to compute modified Red, Green and Blue component values of a pixel in the digital image.

$$B' = C1*(B-\text{Blue peak})*R_f \quad (7)$$

$$R' = C2*(R-\text{Red peak})*B_f \quad (8)$$

$$G' = C3*(G-\text{Green peak}) \quad (9)$$

where R, G, and B are red, green and blue component values of a pixel respectively and R', G', and B' are red, green and blue component values of a modified pixel respectively and C1, C2 and C3 are pre-determined constants. In one embodiment, all of the pre-determined constants have a value of two. However, the present invention is not limited to this embodiment and other constant values can also be used to practice the invention. In addition, the pre-determined constants C1, C2 and C3 do not have to be the same value.

In the Equation (7), a contrast in blue plane pixels is increased. If the pixel has blue component value less than the peak of blue plane, the term (C*B−Blue peak) will be less than B. If the pixel has blue component value greater than the peak of blue plane, the term C*B−Blue peak) will be greater than B. Therefore the difference between two pixel values, one greater than peak and the other less than peak will be increased. A multiplication factor "$R_f$" is used to normalize peak intensity of blue color plane with respect to red color plane peak. A minimum condition used in the equation ensures that the Blue component never exceeds a pre-determined constant X (e.g., 255) and maximum condition used ensures that the Blue component value never becomes negative.

In Equation (8), contrast in the Red plane pixels is increased. If the pixel has Red component value less than the peak of Red plane, the term (C*R−Red peak) will be less than R. If the pixel has Red component value greater than the peak of Red plane, the term (C*R−Red peak) will be greater than R. Therefore the difference between two pixels values, one greater than mean and the other less than mean will be increased. A multiplication factor "$B_f$" is used to normalize peak intensity of red color plane with respect to blue color plane peak A minimum condition used in the equation ensures that the Red component never exceeds a pre-determined constant X, (e.g., 255) and a maximum condition used ensures that the Red component value never becomes negative.

In Equation (9), contrast in the Green plane pixels is increased. If the pixel has Green component value less than the mean of Green plane, the term (C*G−Green peak) will be less than G. If the pixel has Green component value greater than the mean of Green plane, the term (C*G−Green peak) will be greater than Pixel Intensity. Therefore the difference between two pixel values, one greater than peak and the other less than peak will be increased. A minimum condition used in the equation ensures that the Green component never exceeds a pre-determined constant X, (e.g., 255) and a maximum condition used ensures that the Green component value never becomes negative. If a stain is used that has gives an images a green color then a green color ratio $G_f$ would be determined and Equation (9) would include a calculation using a multiplication factor $G_f$ to normalize a peak intensity of an appropriate color plane.

Figure 8:
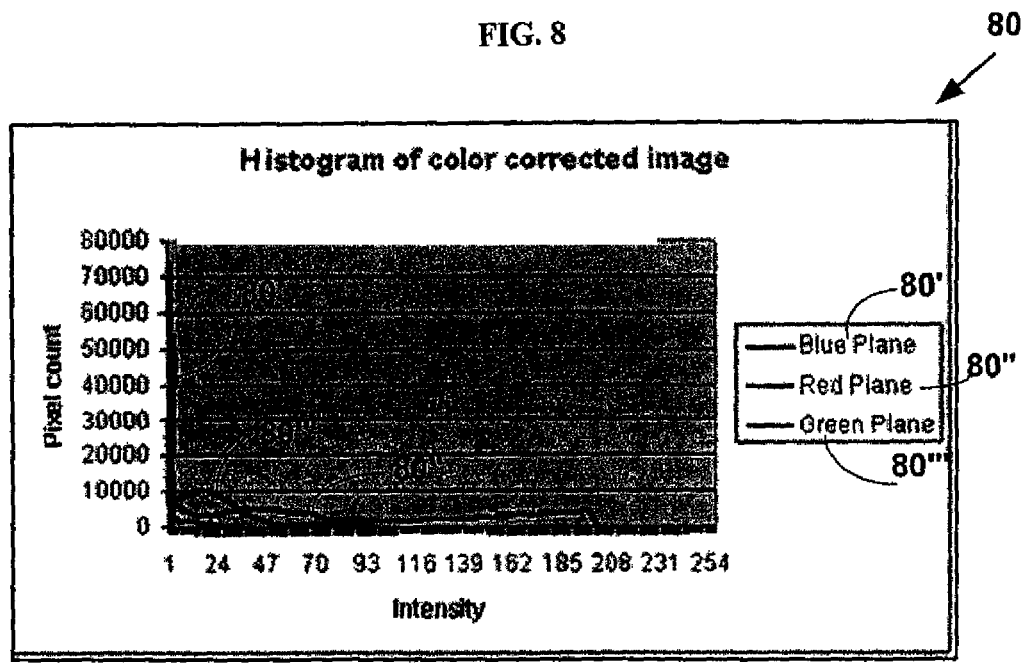
FIG. 8 is a block diagram 80 with a histogram of blue, red and green intensity values calculated from a contrast enhanced digital image.

FIG. 8 is a block diagram 80 with a histogram of blue 80', red 80" and green 80''' color intensity values calculated from the contrast enhanced digital image 78. Note how blue 80' color values have been enhanced compared to red 80" color values.

Returning to FIG. 3 at Step 48, the identified plural cells are segmented using morphological parameters to remove non-motitic cells. In one embodiment, the morphological parameters include cell size, cell elongation, cell component parallelism, degree cell boundary roughness or smoothness and cell shape including convex or concave shapes. However, the invention is not limited to such an embodiment and other morphological parameters can also be used to practice the invention.

In any given tissue sample image, there could be several hundred cells of different types. These cells could be normal epithelial cells, stained epithelial cells, stromal cells or mitotic cells in any one of the mitotic phases. Objects of interest including mitotic cells are segmented and non-mitotic cells are deleted from further processing. One step in segmentation is to locate an object of interest via a thresholding operation. Thresholding is carried out on the modified digital image 78.

Figure 9:
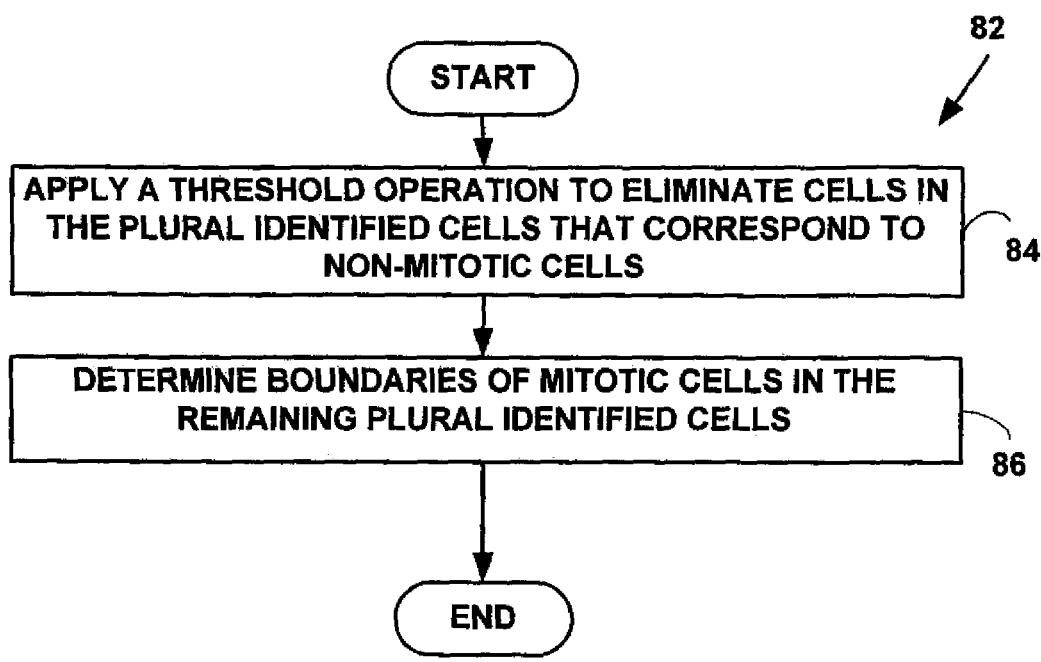
FIG. 9 is a flow diagram illustrating a method for cell object segmentation.

FIG. 9 is a flow diagram illustrating a Method 82 for cell object segmentation. At step 84, a threshold operation is applied to eliminate cells in the plural identified cells that correspond to non-mitotic cells. At Step 86, boundaries of mitotic cells are determined in the remaining plural identified cells.

Method 82 is illustrated with one exemplary embodiment. However, the present invention is not limited to such an embodiment and other embodiments can also be used to practice the invention In such an exemplary embodiment at Step 84, mitotic cells are segmented using thresholding. Using H/E staining, mitotic cells are blue in color and are of different size and shapes than non-mitotic cells. The red and blue color planes of the modified image 78 are used in deciding whether a given pixel belongs to a mitotic cell are not. In one embodiment a threshold value of 20% of a total range of grayscale value of 50 is used for segmenting mitotic cells. However, the present invention is not limited to such a threshold value and other threshold values can also be used to practice the invention.

At Step 86, mitotic cells are cropped to accurate cell boundaries. The mitotic cell boundaries may not be actual mitotic cell boundaries. An area of interest being identified as a mitotic cell is smaller than the actual cell due to hard thresholds being used. Mitotic cells smaller than about 200 pixels in size are deleted and the remaining objects are labeled. Labeled objects are cropped till a relaxed boundary condition is met. Another different threshold is used for cropping mitotic cells to an accurate boundary.

In other embodiment, luminosity of pixels in all color planes is used instead of red plane value to segment mitotic cells.

Figure 10:
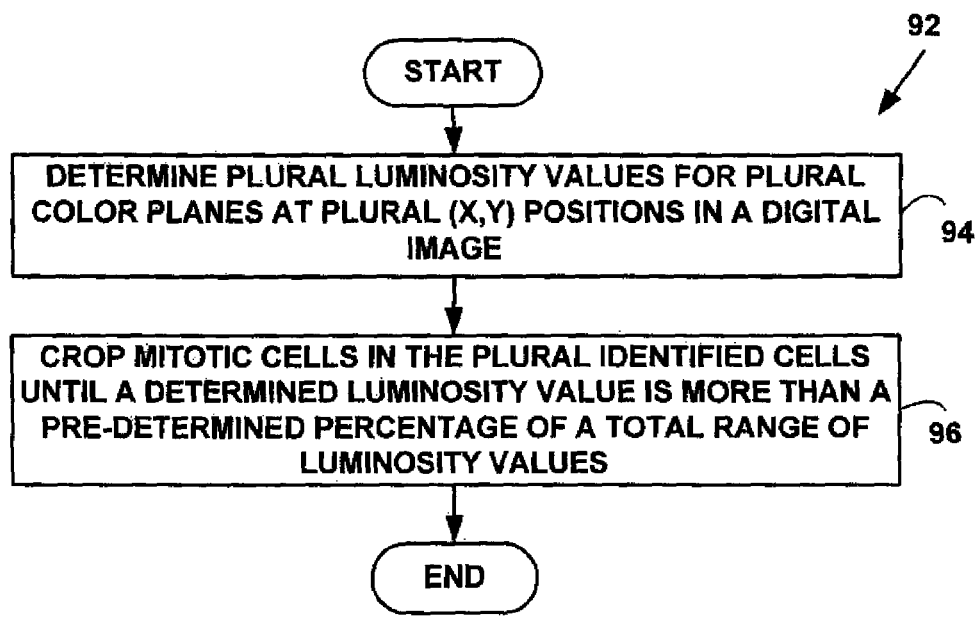
FIG. 10 is a flow diagram illustrating a method for cell object segmentation.

FIG. 10 is a flow diagram illustrating a Method 92 for cell object segmentation. At Step 94, plural luminosity values are determined for plural color planes at plural (x,y) positions in a digital image. At Step 96, mitotic cells in the plural identified cells are cropped until a determined luminosity value is more than a pre-determined percentage of a total range of luminosity values.

Method 92 is illustrated with one exemplary embodiment. However, the present invention is not limited to such an embodiment and other embodiments can also be used to practice the invention.

It is observed that luminosity is less sensitive to staining variations effect on mitotic cell boundaries. At Step 94, to compute a luminosity "I(x,y)" value of a pixel, all three red, green and blue plane values are used in the following Equation(10).

$$I(x,y)=C_1*G(x,y)+C_2*R(x,y)+C_3*B(x,y), \quad (10)$$

where R(x,y), G(x,y) and B(x,y) are red, green and blue plane values at (x,y) position in the digital image 20 respectively. In one embodiment, $C_1$=0.59, $C_2$=0.29 and $C_3$=0.12. However, the present invention is not limited to such an embodiment and other constants can be used to practice the invention. At Step 96, mitotic cells are cropped until a determined luminosity value I(x,y) is more than a pre-determined percentage (e.g., 20%) of a total range of luminosity values (e.g., a value of 50).

In another embodiment, both thresholding and luminosity values are used to segment the identified plural cells.

Figure 11:
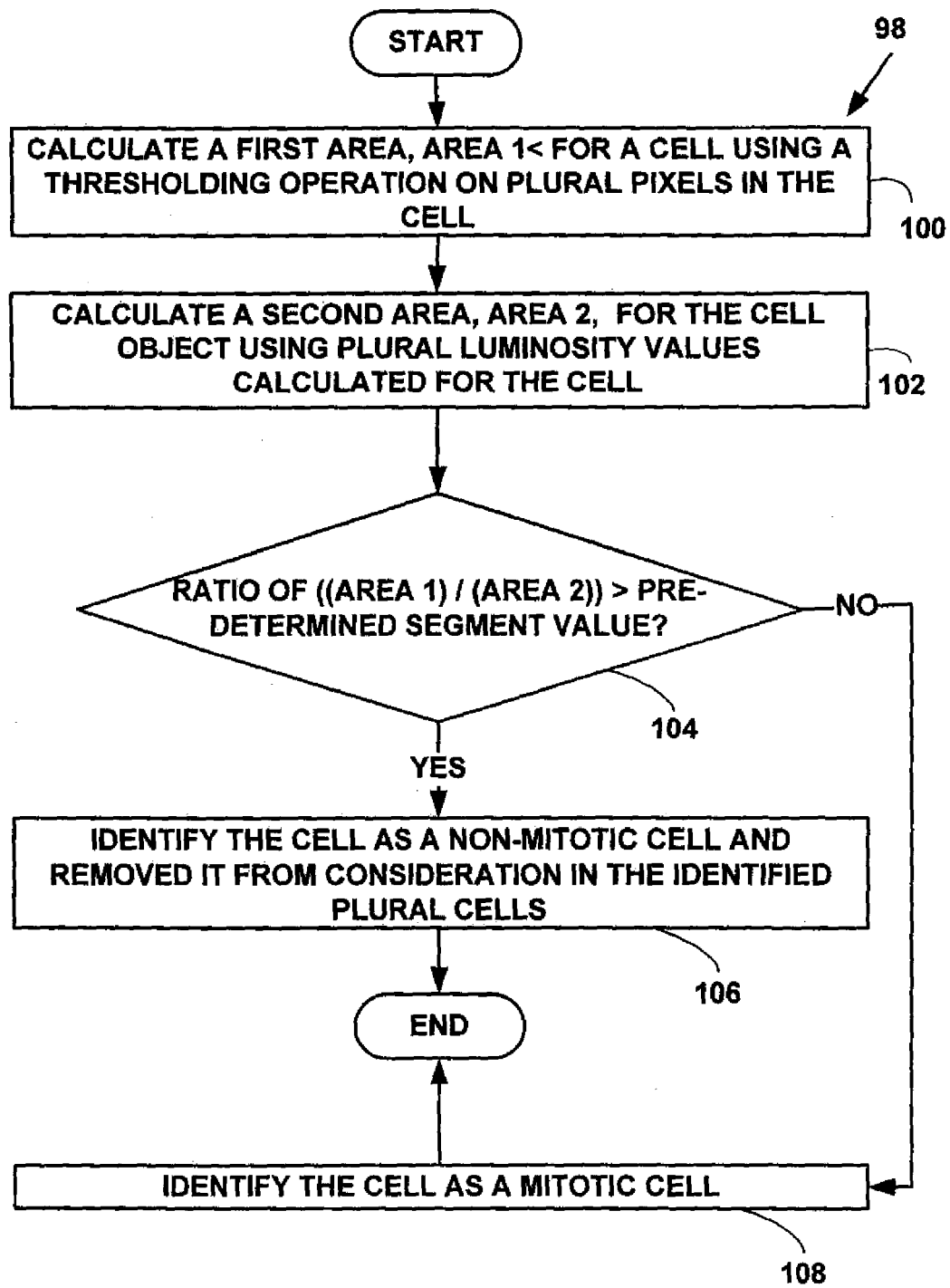
FIG. 11 is a flow diagram illustrating a method for cell object segmentation.

FIG. 11 is a flow diagram illustrating a Method 98 for cell object segmentation. At Step 100 a first area is calculated for a cell using thresholding operation on plural pixels in the cell. At Step 102, a second area is calculated for the cell using plural luminosity values calculated for the cell. At Step 104, a test is conducted to determine whether a ratio of the ((first area)/(second area)) is more than a pre-determined segmenting value, and if so, at Step 106, the cell is identified as a non-mitotic cell and removed from the identified plural cells. If at Step 104 the ratio is less than the pre-determined segmenting value, then at Step 108 the cell is identified as a mitotic cell and not removed from the identified plural cells.

Method 98 is illustrated with one exemplary embodiment. However, the present invention is not limited to such an embodiment and other embodiments can also be used to practice the invention In such an exemplary embodiment, at Step 100, a first area, AREA1, calculated gives an area value which is based on a thresholding operation using red color plane values as was described above in Equations (3-9). At Step 102, a second area, AREA2, is calculated gives an area value based luminosity values of pixels as was describe above for Equation (10) instead of red color plane values. At Step 104, If the ratio, AREA1/AREA2 is more than the pre-determined segmenting value (e.g., 0.55), then at Step 102, the cell object is identified as non-mitotic. In one embodiment, a pre-determined value of 0.55 is used. However, the present invention is not limited to such an embodiment and other pre-determined segmenting can also be used to practice the invention. If at Step 104 the ratio is less than the pre-determined segmenting value, then at Step 108 the cell is identified as a mitotic cell and not removed from the identified plural cells.

Returning to FIG. 3 at Step 50 plural mitotic cells are identified from the segmented plural cells. In one embodiment, plural filters are used to identify mitotic cells. Table 6 illustrates exemplary filters applied to identify mitotic cells of interest. However, the present invention is not limited to the steps illustrated in Table 6 and other filters can also be used to practice the invention.

TABLE 6

Size based filter
Elongation ratio based
Parallelism based filter
Convex hull based filter
Shape based filter
Boundary smoothness filter Size based filters: In any given tissue sample image, there could be several hundred cells, but there typically will be only a small number of mitotic cells. Mitotic cells are larger than normal cells and are often larger than 15 microns. At standard resolution of 40×, a 15-micron object corresponds to about 300 pixels. Artifacts and blood vessels are very big compared to mitotic cells. Large artifacts and blood vessels are filtered by limiting the size to 100 microns or 10000 pixels at 40× resolution. Size based filters are used to filter away such large artifacts. One more stage of size-based filtering then is used to filter mitotic cell objects.

Even amongst the mitotic cell objects that satisfy above size limits, mitotic cell size is always above average cell size. Mitotic cell objects less than an average size are removed for further processing. While utilizing the information that mitotic cells are larger than normal cells, pathologists seldom use numbers attached to these terms. Terms like "large" are always relative.

In the present invention, a size of mitotic cells objects in terms of pixels is used for identification as belonging to a Telophase 34 mitotic activity. In one embodiment, large artifacts are filtered by limiting object size to 1500 pixels at 40× resolution. In such an embodiment, if any two objects have size more than 1500 pixels, then this pair of cell objects cannot belong to Telophase 34 mitotic cell. However, the present invention is not limited to such an embodiment and other object sizes can also be used to practice the invention.

Elongation ratio based filters: At two stages of the evolution, namely, Prophase 28 and Metaphase 30, mitotic cells exhibit elongated dumb bell shape. An "elongation ratio" is defined as a ratio of major axis over minor axis. This ratio is used in determining an object shape factor of a cell. In order to compute elongation ratio, a center of a cell object is determined. A major axis is determined by computing a length of the object in all directions passing through a center of the object. A length and angle of a maximum length line passing through a center of the object gives major axis and angle of major axis. Minor axis is considered to be perpendicular to the major axis. The minor axis is determined based on line passing through the center of the object and perpendicular to the major axis. However, other calculations can also be used to calculate an elongation ration and this embodiment.

In one embodiment, an exemplary elongation ratio of 1.5 is used to eliminate circular objects is used. However, the present invention is not limited to this ratio and other access ratios can also be used to practice the invention.

Elongation ratios are checked. If an object has an aspect ratio much larger than one, this means its length is twice the width. This is more likely a mitotic cell. On the other hand, if the aspect ratio is one or less, then the object is circular or nearly circular in shape. These circular objects are not part of a Telophase 34 mitotic cell. In one embodiment, if any of these two objects have aspect ratio value less than 1.5, then this pair of objects cannot belong to Telophase 34 mitotic cell.

Mitotic cells are typically very long compared to normal cells, in particular mitotic cells in Metaphase 30 a length of major axis will be very high. Non-mitotic cells are filtered using length of a major axis. In one embodiment, an exemplary hard threshold value of 85 pixels is used for length of major axis to filter non-mitotic cells. However, the present invention is not limited to such an embodiment and other embodiments can also be used to practice the invention.

Size of a mitotic cell image does not vary on re-segmentation with a relaxed threshold. Therefore a ratio of size of an object with hard threshold and relaxed threshold can also be used to filter non-mitotic cells.

Another important characteristic of mitotic cells in Telophase 34 is that two components of a mitotic cell are well separated and are parallel. So a parallelism property of two identified mitotic cells is used to identify mitotic cells.

Parallelism based filter: Cell objects that are not parallel because of a difference in proximity size, width, length and elongation are detected. Parallelism based filters are used.

A proximity of two separate objects is used to determine if the pair belongs to Telophase 34 mitotic cell or not. During Telophase 34, two separate mitotic cells are still in close proximity and are not migrated to other parts of tissue Euclidian distance between two mitotic cells is used to estimate the proximity. In order to facilitate variations in sizes of mitotic cells, in one embodiment a pre-determined proximity threshold limit of four times a maximum length L of the two objects is used. A pair of mitotic cells farther than this pre-determined proximity threshold limit cannot belong to Telophase 34. However, the present invention is not limited to such an embodiment and other pre-determined proximity threshold limits can also be used to practice the invention.

A difference in a length "L" of cell objects is used to identify Telophase 34 mitotic cells. Both parts of mitotic cells in Telophase 34 are supposed to be a same length as these are created from a single cell. A pair of cell objects can be considered as two components in Telophase 34 if the difference in their length is less than a pre-determined length threshold of a cell object having maximum length in a pair under consideration. In one embodiment, the pre-determined length threshold of 30% is used for difference in length to eliminate non-Telophase 34 mitotic cells. However, the present invention is not limited to such an embodiment and other pre-determined length thresholds can also be used to practice the invention.

A difference in a width "W" of cell objects is used to identify Telophase 34 mitotic cells. Both parts of mitotic cells in Telophase 34 are supposed to be of the same width as these are created from a single cell. A pair of objects can be considered as two components in Telophase 34 if a difference in their width is less than a pre-determined percentage of an object having maximum width in a pair of objects under consideration. In one embodiment, a pre-determined width threshold of 30% is used for difference in width to eliminate non-Telophase 34 mitotic cells. However, the present invention is not limited to such an embodiment and other pre-determined width thresholds can also be used to practice the invention.

A difference in the size "S" of objects is used to identify Telophase 34 mitotic cells. Both parts of mitotic cells in Telophase 34 are supposed to be of the same size as these are created from a single cell. A pair of objects can be considered as two components in Telophase 34 if a difference in their size is less than a pre-determined percentage of the object having maximum size in the pair under consideration. In one embodiment, a pre-determined size threshold of 30% is used to determine a difference in size to eliminate non-Telophase 34 mitotic cells. However, the present invention is not limited to such an embodiment and pre-determined size thresholds can also be used to practice the invention.

A number of parameters are used in determining if two given mitotic cells are parallel and close enough to be classified as Telophase 28. A first parameter $P_1$ is illustrated in Equation (11):

$$P_1 = (E_1, L_1, \text{Theta}_1, W_1, S_1) \quad (11)$$

where $E_1$ is an elongation ratio, $L_1$ is a length of a major axis, Theta₁ is an angle of major axis with a X-axis, $W_1$ is a width of object₁ at the center of object and $S_1$ is a size of object₁.

A second parameter $P_2$ is illustrated in Equation (12):

$$P_2 = (E_2, L_2, \text{Theta}_2, W_2, S_2) \quad (12)$$

where $E_2$ is an elongation ratio, $L_2$ is a length of a major axis, Theta₂ is an angle of major axis with a X-axis, $W_2$ is a width of object2 at the center of object₁ and S $S_2$ is a size of object₁.

Cell objects one and two can be classified as mitotic cells if the conditions listed in Table 7 are satisfied for standard images at 40× resolution. However, the present invention is not limited to the conditions in Table 7 and more, fewer or other conditions can also be used to practice the invention.

TABLE 7

$E_1 > 1.5$ and $E_2 > 1.5$
$S_1 < 1500$ and $S_2 < 1500$
Difference between an angle of major axis, Theta₁ and Theta₂ is less than 25 degrees.
Distance between the centers of the two objects is less than four times a maximum of $L_2$ and $L_2$, where the distance is a Euclidean distance between the centers of the objects.
Difference in Size S is less than 30% of either of the objects.
Difference in Length L of objects is less than 30% of either of the objects length.
Difference in Width W of objects is less than 30% of either of the objects width.
Angle Beta between the line joining two centers and the major axis should not be less than 65 degrees, where Beta is an angle between a line joining the two centers and the major axis.

A difference in of major axis of two objects is used to decide the parallel nature of mitotic cells in Telophase 34. Theta₁, indicates an angle of a major axis of object one makes with an x-axis. Theta₂, indicates a angle major axis of object two makes with the x-axis. The difference in angles will be negative if Theta is less than Theta₂. Therefore an absolute value is used. In one embodiment, if the difference in angles of major axis is less than 25 degrees, then this pair of objects belongs to Telophase 34 mitotic cell. In this embodiment, a threshold angle of 25 degrees is used for difference in angle to eliminate non-parallel mitotic cell pairs. However, the present invention is not limited to this threshold angle and other angles can also be used to practice the invention.

Parallelism is also measured by finding a difference between an angle Beta of a line joining the centers of the two objects and a major axis of both objects separately. A maximum of the difference is one factor used to determine if a pair of objects is parallel or not. In one embodiment, ideally the angle Beta is 90 degrees. However, in reality this angle Beta could be much less than 90 degrees. In another embodiment a threshold angle Beta of 65 degrees is used for deciding if the pair of objects are parallel. However, the present invention is not limited to such an embodiment and other threshold angles can also be used to practice the invention.

In Prophase 28 of mitotic cell division, a boundary of mitotic cell undergoes a major change. It develops a convex shape before splitting into two dumb bell shaped cells. A convex hull property is used to identify convexity of mitotic cells.

Convex hull based filter: Convex hulls are also features of a mitotic cell. Normal cells are concave in shape. A ratio of convex hull pixels is measured to a size of the object in order to distinguishing between mitotic cells and dying cells (e.g., crimped). Dying cells, which are crimped, have convex hulls, but this convex hull ratio will be very large.

As is known in the art convex hull have been used for boundary description in digital images. However, most convex hulls known in the art use a change in slope for detecting a convex hull boundary. For example, R. C. Gonzalez, and R. E. Woods in "Digital Image processing," Pearson Education, 2003 pp. 653-655 describe a method using a change in slope for detecting a convex hull boundary.

In the current embodiment, a neighborhood based operator is used instead of a change in slope to detect a convex hull boundary. Neighborhood based operations on binary images are faster and more efficient compared to sequential operations like finding slope at a pixel. All identified mitotic cells are considered as two level image objects and analyzed for a convex hull part. In one embodiment, neighborhood operations are implemented using a pre-determined size neighborhood mask (e.g., 3×3).

Figure 12:
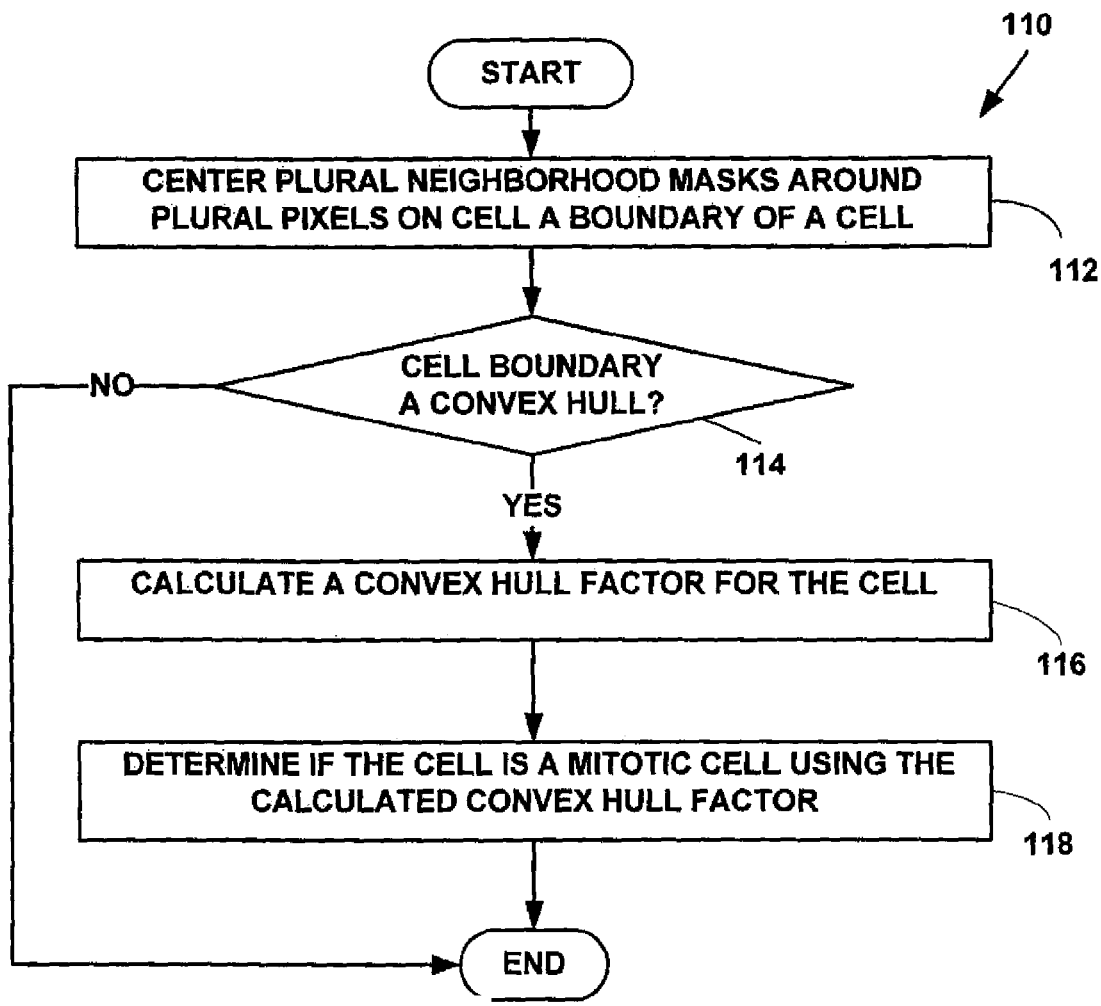
FIG. 12 is a flow diagram illustrating a method determining a convex hull part of a mitotic cell boundary in a digital image.

FIG. 12 is a flow diagram illustrating a Method 110 for determining a convex hull part of a mitotic cell boundary in a digital image. At Step 112, plural neighborhood masks are centered around plural pixels on a boundary of a cell. At Step 114, a test is conducted to determine if the pixels belong to a convex hull boundary of the cell. If the cell boundary is a convex hull of the cell at Step 114, a convex hull factor is calculated for the cell at Step 116. At Step 118, the calculated convex hull factor is used to determine if the cell is a mitotic cell.

Method 110 is illustrated with one exemplary embodiment. However, the present invention is not limited to such an embodiment and other embodiments can also be used to practice the invention.

Figure 13:
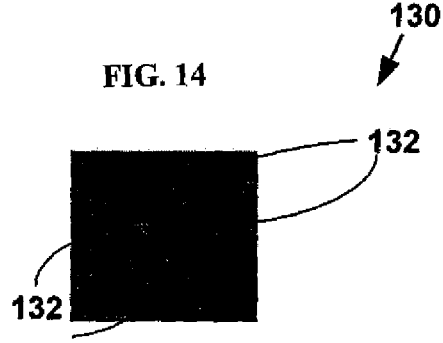
FIG. 13 is a block diagram of neighborhood masks used to determine a convex hull part in a mitotic cell boundary.

In such an exemplary embodiment, at Step 110 plural pixel neighborhood masks are centered around every pixel on a boundary of a cell object to determine if the pixels belong to a convex hull of the cell object FIG. 13 is a block diagram 120 of exemplary neighborhood masks, 122, 124, 126, 128 used to determine a convex hull part in a mitotic cell boundary. However, the present invention is not limited to these neighborhood masks and other neighborhoods masks can be used to practice the invention.

In one embodiment, at Step 112 a neighborhood mask (e.g., 3.times.3) is centered around every pixel on a boundary of a cell object to determine if the pixel belongs to a convex part of the cell object. A cell object in this context is a two level image, where a value one implies it is a pixel on a mitotic cell and a value zero implies it is a pixel not on the mitotic cell. A pixel with value zero having three neighbors all with value one is identified as a pixel in the convex hull of the object. There are four variations in the neighborhood mask pattern to accommodate the possible permutations as is illustrated in FIG. 13. In one embodiment, a pixel is identified as pixel on convex hull part of boundary if it satisfies any of the neighborhood masks 122-128. However, the present invention is not limited to this embodiment and other embodiments can also be used to practice the invention.

Returning to FIG. 12 at Step 114, if the cell boundary is a convex hull of the cell boundary, at Step 116 a ratio of pixels is used satisfying convex hull condition over the cell object size. Let $H_f$ be the convex hull factor defined as is illustrated in Equation (13).

$$H_f = \text{(number of pixels on a convex hull)/(number of pixels in a cell)} \quad (13)$$

At Step 118, if a cell object has $H_f$ in a range of about 0.05 to 0.70, then the cell object is a mitotic cell. If $H_f$ is less than about 0.05, it means that the cell object is concave in nature (i.e., a non-mitotic or "normal" cell). If $H_f$ is more than about 0.70 then the cell object is has a very large hull part (i.e., the cell is crimped and dying). However, the present invention is not limited to such $H_f$ values and other $H_f$ values can also be used to practice the invention.

Shape Base Filter: During Metaphase 30 and Telophase 34 stages of the cell division, mitotic cells exhibit elongated dumb bell shape. This shape factor is reliable means of classifying mitotic cells. A dumb bell shape is used to identify mitotic cells. A ratio of a major axis over minor axis is used in determining the object shape factor of a mitotic cell. In order to compute elongation ratio, a center of the object is determined first by finding the mean values of x and y coordinates of all pixels in the object. A major axis is determined by computing a length of the chords in all directions passing through the center of the object. A length and angle of a maximum length chord passing through the center of the object gives major axis and angle of major axis. A minor axis is considered to be perpendicular to the major axis. The minor axis is determined based on line passing through a center of the object and perpendicular to the major axis. An elongation ratio, defined as the ratio of major axis over minor axis is determined. In the current embodiment, a pre-determined shape threshold of 1.5 is used for the elongation ratio to eliminate circular objects. However, the present invention is not limited to such an embodiment and other pre-determined shape thresholds can also be used to practice the invention Boundary Smoothness Filter: Mitotic cells have different characteristic during Prophase 28 including checkered boundary with a number of thread like extensions. Boundary smoothness factor is used to filter objects that exhibit rough boundaries. Segmented objects which are binary in nature are considered for analysis. Objects under consideration are eroded by one pixel thickness. Subtracting an eroded object from an original object provides an object boundary. It is observed that a standard operation like smoothening digital image by applying low pass filter like Gaussian operator eliminates high frequency variations in a boundary and gives an estimation of boundary roughness. A Gaussian filter is applied to create a smoothened version of the identified object. A boundary of a smoothened object under consideration is determined by eroding the object by one pixel thickness and then subtracting eroded object from the original.

A center of gravity of the identified object boundary is determined by finding the sum of all x coordinates of pixels on a boundary "Xsum," finding the sum of all y coordinates of pixels on the boundary "Ysum." An X coordinate of the center of gravity can be calculated by dividing Xsum by a number of pixels on the boundary. Similarly, a Y coordinate of the center of gravity can be calculated by dividing Ysum by the number of pixels on the boundary. Boundary roughness is calculated based on a difference in distance between the center of gravity and pixels on the two boundaries, namely one without Gaussian smoothening and the other with Gaussian smoothening. In one embodiment, 360 pixels on boundary are considered for calculating boundary roughness. However, the present invention is not limited to such an embodiment and more or fewer pixels can be used on a boundary and other boundary calculations can also be used to practice the invention.

A difference in distance will be of same sign, either positive or negative for circular objects, but will have several changes in sign for objects with convex hulls. The number of times the difference in distance changes sign indicates a boundary roughness value. A given object is identified as mitotic if any of the following three Equations (16), (17), (18) are satisfied. Let "Texture Roughness" be a number of times a sign changes, "Structural Roughness," be a number of large projections on the object boundary, and "Number of common segments" be a number of segments which are common between the two boundaries.

$$\text{Texture Roughness} > R_1 \qquad (16)$$

$$\text{Texture Roughness} + \text{Structural Roughness} > R_2 \qquad (17)$$

$$\text{Texture Roughness} + \text{Structural Roughness} + \text{number of Common Segments} > R_3 \qquad (18)$$

wherein $R_1$ is a first constant (e.g., 4.0), $R_2$ is a second constant (e.g., 7.0) and $R_3$ is a third constant (e.g., 10). However, the present invention is not limited to these constants and other constants can also be used to practice the invention.

Prophase 28 mitotic cell exhibits rough boundary at a local level, Metaphase 30 mitotic cells exhibit smooth boundary on global level. Objects that have a smooth boundary but are not mitotic are filtered.

A boundary smoothness factor is determined. Segmented objects which are binary in nature are considered for analysis. Objects under consideration are eroded by one pixel thickness. Subtracting eroded object from the original gives object boundary. Pixels on an object boundary are chain coded using 8-connectivity. Chain coding and 8-connectivity are extensively covered in the literature including the text book "Digital Image Processing" by Gonzalez R C, and Woods R E, Pearson Education, 2003. Isolated noise on the chain code is eliminated. A difference in chain code between adjacent pixels on the object boundary is calculated. This difference varies between zero and seven. For a linear portion of any curve, this difference between adjacent pixels will be zero. Therefore by calculating the ratio of number of pixels with zero difference in chain code to the total number of pixels on the boundary a measure of boundary smoothness is determined.

Returning to FIG. 3, at Step 52, the plural mitotic cells are classified using a pre-determined classification scheme to create a medical diagnosis or prognosis. In one embodiment, the pre-determined classification scheme includes a Nottingham grading system or counting a number of mitoses in ten high power fields (HPFs) that is used to classify the mitotic cells. However, the present invention is not limited to such an embodiment and other pre-determined classification schemes or systems can be used to practice the invention. In one embodiment, a medical diagnosis may include a diagnosis of N-stage breast cancer or a medical prognosis such as terminal breast cancer with six months to live.

In one exemplary set of actual results of using Method 44 to automatically identify mitotic cells in a digital image, an experienced pathologist with ten years of experiences was shown results of the method. The experienced pathologist manually identified only eight mitotic cells.

Method 44 was executed on a digital image. Method 44 automatically identified seventeen mitotic cells. There were 17 actual cells undergoing mitosis.

TABLE 7

| Mitotic cells manually Identified by human pathologist | Mitotic cells Identified by Automated Method 44 | Mitotic cells not identified By pathologist Error % | Mitotic cells not identified by Automated Method 44 Error % |
| --- | --- | --- | --- |
| 8 | 17 | 47% | 0% |

Thus, automated Method 44 determined all mitotic cells including many missed by a pathologist performing manual methods.

FIG. 15 is a block diagram illustrating an exemplary flow of data 142 in the automated digital image based mitosis detection and classification system 10. Pixel values from a digital image 20 of a biological sample to which a chemical compound has been applied are captured 144 as raw digital images 146. The raw digital images 146 are stored in raw image format in one or more image databases 22. Luminance and morphological parameters from individual biological components within the biological sample are analyzed on the digital image and modifications made to the raw digital images are used to create new biological knowledge 148 using the methods described herein. The new biological knowledge is stored in a knowledge database 150. Peer review of the digital image analysis and life science and biotechnology experiment results is completed 152. A reference digital image database 154 facilitates access of reference images from previous records of life science and biotechnology experiments at the time of peer review. Contents of the reference digital image database 154, information on the biological sample and analysis of current biological sample are available at an image retrieval, reporting and informatics module 156 that displays information on GUI 14. Conclusions of a medical diagnosis or prognosis or life science and biotechnology experiment are documented as one or more reports. Report generation 158 allows configurable fields and layout of the report. New medical knowledge is automatically created and saved.

Automatic Neural Network Based Mitosis Cell Classification

In one embodiment of the invention, the methods and systems described herein are completed within an Artificial Neural Networks (ANN). An ANN concept is well known in the prior art. Several text books including "Digital Image Processing" by Gonzalez R C, and Woods R E, Pearson Education, pages 712-732, 2003 deals with the application of ANN for classification of patterns.

In one embodiment, an ANN based on FIG. 15 is used for training and classifying mitotic cells from plural biological samples analyzed over time. In the classification mode, a given cell input object is classified as mitotic or non-mitotic based on three parameters values. These parameters are a gradient variation within a cell object, cell object boundary irregularity and cell object elongation ratio as was discussed above. However, more, fewer or other parameter may also be used to practice the invention.

Figure 16:
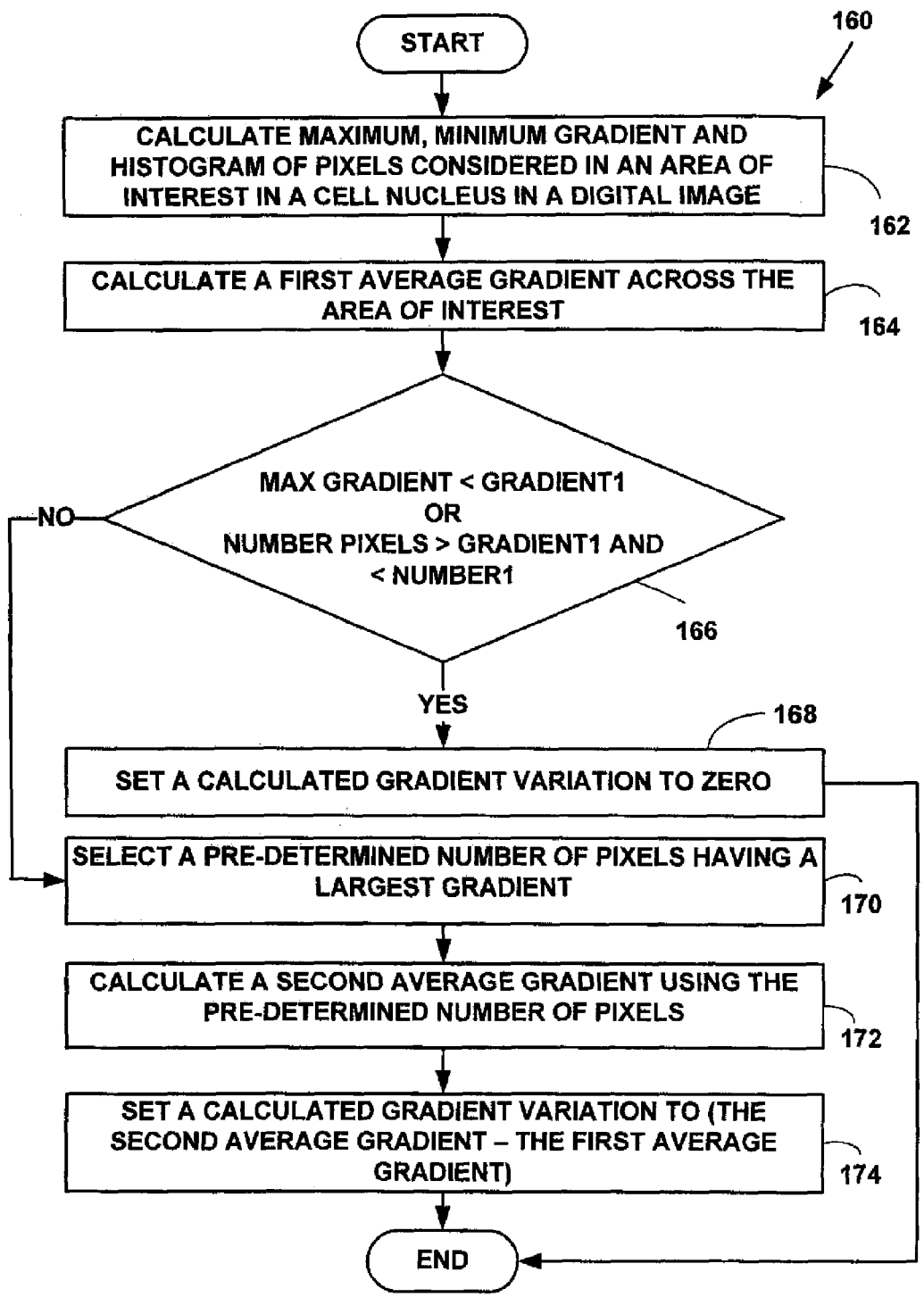
FIG. 16 is a flow diagram illustrating a method for determining a gradient within a cell nucleus.

FIG. 16 is a flow diagram illustrating a Method 160 for determining a gradient with a cell nucleus. At Step 162, a minimum and maximum gradient in an area of interest of a cell nucleus in a digital image and a histogram of the gradient of corresponding pixels used are calculated. At Step 164, a first average gradient across the area of interest is calculated. At Step 166, a test is conducted to determine if the calculated maximum gradient is less than a pre-determined gradient or a pre-determined number of pixels with a gradient greater then the pre-determined gradient is less than a pre-determined number, then at Step 168, a calculated gradient variation is set to zero. Otherwise at Step 170, a pre-determined number of pixels having a largest gradient are selected. At Step 172, a second average gradient variation is determined. At Step 174, a calculated gradient is set to (second average gradient-first average gradient).

Method 160 is illustrated with one exemplary embodiment. However, the present invention is not limited to such an embodiment and other embodiments can also be used to practice the invention.

In such an exemplary embodiment at Step 162. Minimum and maximum gradients in an of area interest in a cell nucleus and a histogram of the gradient of corresponding pixels used are calculated. At Step 164, a first average gradient, AVG1, across the area of interest is calculated. At Step 166, a test is conducted to determine a gradient variation within the cell nucleus. At Step 168, if a maximum gradient is less than a pre-determined gradient1 (e.g., 20), or a number of pixels with a gradient more than the pre-determined gradient1 is less than a pre-determined number1 (e.g., 10), then a calculated gradient variation is set to zero at Step 170. Otherwise, a second average gradient, AVG2, for selected pixels is calculated at Step 172. In one embodiment, for computing AVG2, a pre-determined number (e.g., 20) pixels having largest a gradient are selected. This selection is done based on the histogram of the gradient within nucleus calculated at Step 162. At Step 174, the calculated gradient variation is set to (AVG2−AVG1). This value indicates a variation in gradient within the cell nucleus. This value along with other two features is used by artificial neural network for classifying object as mitotic or non-mitotic.

In the exemplary embodiment described, the pre-determined gradient1 includes a value of 20, the pre-determined number1 includes a value of 10, the pre-determined number of pixels having a largest gradient includes a value of 20. However, the present invention is not limited to these values and values can also be used to practice the invention.

Figure 17:
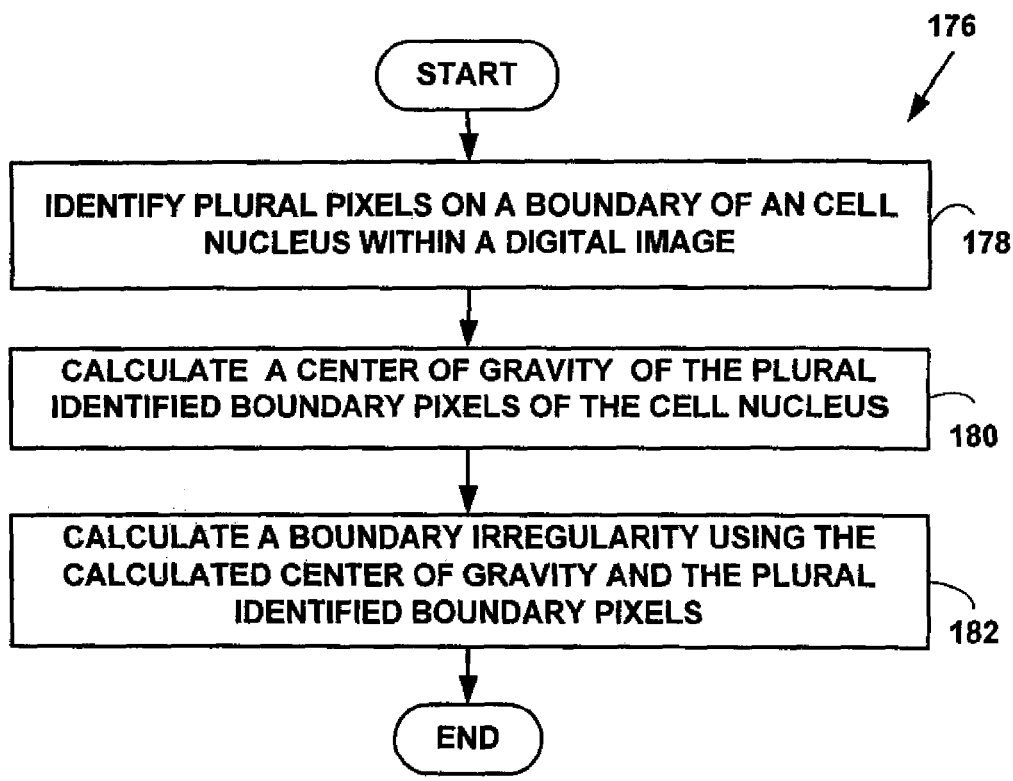
FIG. 17 is a flow diagram illustrating a method for determining boundary irregularity for a cell nucleus.

FIG. 17 a flow diagram illustrating a Method 176 for determining boundary irregularity for a cell nucleus. At Step 178, plural pixels on a boundary of cell nucleus in a digital image are identified. At Step 180, a center of gravity of the identified plural boundary pixels is calculated. At Step 182, a boundary irregularity is calculated using the computer center of gravity and the identified plural boundary pixels.

Method 176 is illustrated with one exemplary embodiment. However, the present invention is not limited to such an embodiment and other embodiments can also be used to practice the invention.

In such an exemplary embodiment at Step 178, cell nuclei segmented with one or more of the segmenting methods described above which are binary in nature are considered for analysis. A cell nucleus under consideration is eroded by one pixel thickness. Subtracting eroded cell nucleus pixels from the original cell nucleus gives an object boundary.

At Step 180, a center of gravity of the identified cell nucleus boundary is calculated by finding a sum of all x coordinates of pixels on the boundary, Xsum, finding a sum of all y coordinates of pixels on the boundary, Ysum. An "x" coordinate of the center of gravity can be calculated by dividing Xsum by a number of pixels on the boundary. Similarly, a "y" coordinate of the center of gravity can be calculated by dividing Ysum by the number of pixels on the boundary.

At Step 182, a boundary irregularity is calculated based on the variation in distance between the center of gravity and pixels on the boundary. In one embodiment, pixels on boundary at an interval of 5 degrees are considered for calculating boundary irregularity. This distance will be constant for circular objects, but will have several zero crossings for objects with convex hulls. Zero crossing is with respect to average distance between the center of gravity and pixels on the boundary. The number of times the distance value is making a zero crossing indicates the boundary irregularity value. However, the present invention is not limited to these degree value or distances and values can also be used to practice the invention. This boundary irregularity is also used by the ANN for classifying object as mitotic or non-mitotic.

In one embodiment, an ANN with back propagation network with one hidden layer is used to practice the invention using the methods and systems described herein. However, the present invention is not limited to such an embodiment and other embodiments can also be used to practice the invention. In such an embodiment, the ANN is trained for a maximum of 5000 cycles or a threshold on average error. In such an embodiment, an average error of 0.01 is used for terminating training. However, the present invention is not limited to such an embodiment and other embodiments can also be used to practice the invention.

The present invention is implemented in software. The invention may be also be implemented in firmware, hardware, or a combination thereof, including software. However, there is no special hardware or software required to use the proposed invention.

The methods and system described herein are used to provide an automated medical conclusion or a life science and biotechnology experiment conclusion is determined from the analyzed luminance and morphological parameters of mitotic cells. The method and system is also used for automatically obtaining a medical diagnosis (e.g., a carcinoma diagnosis) or prognosis. The method and system may also be used to provide an automated medical conclusion for new drug discovery and/or clinical trials used for testing new drugs.

It should be understood that the architecture, programs, processes, methods and systems described herein are not related or limited to any particular type of computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

While various elements of the preferred embodiments have been described as being implemented in software, in other embodiments hardware or firmware implementations may alternatively be used, and vice-versa.

The claims should not be read as limited to the described order or elements unless stated to that effect. In addition, use of the term "means" in any claim is intended to invoke 35 U.S.C. §112, paragraph 6, and any claim without the word "means" is not so intended.

Therefore, all embodiments that come within the scope and spirit of the following claims and equivalents thereto are claimed as the invention.

We claim:

1. An automated method for mitosis cell analysis, comprising:

analyzing luminance values from a plurality of pixels in a digital image of a biological tissue sample comprising one or more human cancer cells to which a chemical compound comprising a Haematoxylin and Eosin stain has been applied and adjusting the luminance values if necessary, to identify a plurality of cells;

segmenting the identified plurality of cells using morphological parameters to remove non-mitotic cells;

identifying a plurality of mitotic cells from the segmented plurality of cells; and classifying and displaying the identified plurality of mitotic cells with a pre-determined classification scheme to create a medical diagnosis or prognosis;

wherein the segmenting step includes: calculating a first area for a cell from the identified plurality of cells using a thresholding operation on a plurality of pixels in the cell;

calculating a second area for the cell using a plurality of luminosity values calculated for the cell; and determining whether a ratio of the ((first area)/(second area)) is more than a pre-determined segmenting value, and if so, identifying the cell as a non-mitotic cell and removing the cell from consideration in the identified plurality of cells; wherein the classifying step includes: extracting cell features from the identified plurality of mitotic cells; and classifying the identified plurality of mitotic cells using a trained artificial automated neural network; wherein the analyzing step includes a pre-processing procedure using a computing device comprising:

determining a minimum pixel intensity in a plurality of color planes in the digital image; and adjusting luminance parameters using the determined minimum pixel intensity within one or more determined areas of interest to create one or more adjusted areas of interest to contrast enhance pixels within the digital image.

2. The method of claim 1 further comprising providing a computer readable medium having stored therein instructions for one or more processors to execute the steps of the method.

3. The method of claim 1 wherein the one or more human cancer cells are breast cancer cells.

4. The method of claim 1 wherein the morphological parameters include cell size, cell elongation, cell component parallelism, cell boundary roughness or smoothness and cell shape including convex or concave cell shapes.

5. The method of claim 1 wherein the step of determining minimum pixel intensity includes determining a minimum pixel intensity of a digital image based on digital image statistics and the adjusting step includes correcting color components of selected pixels within the determined areas of interest using the determined minimum pixel intensity.

6. The method of claim 5 wherein the determining step includes computing histograms of pixel values for each color plane independently in a digital image and determining a minimum intensity of an active range of pixels using a distribution of pixel values from the calculated histograms in each of plural color planes independently.

7. The method of claim 1 wherein the segmenting step includes:

applying a threshold operation to the identified plurality of cells to eliminate cells that correspond to non-mitotic cells; and determining the boundary of each of the mitotic cells in the remaining identified plurality of cells.

8. The method of claim 1 wherein the segmenting step includes applying a threshold operation on the digital image based on pixel values of cells in a red color plane.

9. The method of claim 1 wherein the segmenting step includes:

determining a plurality of luminosity values of a plurality of pixels at a plurality of positions in the digital image in a plurality of color planes of the digital image; and cropping the identified plurality of cells until a determined luminosity value is more than a pre-determined percentage of a total range of luminosity values.

10. The method of claim 1 wherein the step of identifying a plurality of mitotic cells from the segmented plurality of cells includes identifying plurality of mitotic cells from the segmented plurality of cells by applying one or more filters.

11. The method of claim 10 wherein the one or more filters include a size based filter, a shape based filter, an elongation ratio based filter, a parallelism based filter, a convex hull based filter, or boundary smoothness filter.

12. The method of claim 11 wherein applying the convex hull based filter includes:

centering a plurality of neighborhood masks around a plurality of pixels on a boundary of a cell from the segmented plurality of cells; and determining whether the plurality of pixels on the boundary of the cell belong to a convex hull of the cell, and if so, calculating a convex hull factor is calculated for the cell, and determining if the cell object is a mitotic cell using the calculated convex hull factor.

13. The method of claim 12 wherein the step of calculating a convex hull factor includes calculating a convex hull factor $H_f$: $H_f=((\text{number of pixels on the convex hull of the cell})/(\text{number of pixels in the cell}))$.

14. The method of claim 1 wherein the step of identifying a plurality of mitotic cells from the segmented plurality of cells includes:

identifying mitotic cells based on an applied pre-determined size threshold;

identifying mitotic cells based on calculated shape factor;

identifying mitotic cells based on a calculated parallelism to other mitotic cells;

identifying mitotic cells based on a calculated elongation ratio;

identifying mitotic cells based on a computer convex hull factor; and identifying mitotic cells based on a calculated boundary smoothness.

15. The method of claim 14 wherein calculating the shape factor includes:

determining a center of a mitotic cell;

determining a major axis and its angle for the mitotic cell;

determining a minor axis for the mitotic cell; and calculating a ratio of major axis over minor axis to compute the shape factor for the mitotic cell.

16. The method of claim 14 wherein calculating parallelism includes:

comparing shape factors of two mitotic cells with a pre-determined threshold;

comparing a size of each mitotic cell against pre-determined limits;

comparing a Euclidian distance between the centers of two mitotic cells;

comparing differences in angles of major axes with respect to a fixed axis; and comparing a ratio of widths of both mitotic cells.

17. The method of claim 14 wherein calculating the boundary smoothness includes:

identifying pixels on a convex hull for a mitotic cell;

calculating a ratio of the convex hull area to an area for the mitotic cell; and filtering mitotic cells based on the calculated ratio of convex hull area to the mitotic cell area.

18. The method of claim 1 wherein the classifying step includes classifying the identified plurality of mitotic cells based on mitotic activity and mitotic phase.

19. The method of claim 1 wherein the extracting step includes:
calculating a gradient variation of a cell nucleus within a cell of interest;
calculating a boundary irregularity of the cell nucleus; and
calculating a length to breadth elongation ratio of the cell nucleus.

20. The method of claim 1 further comprising:
generating one or more reports related to the medical diagnosis or prognosis; and
presenting the digital image and one or more generated reports for the medical diagnosis or prognosis on a graphical user interface.

21. An automated method for mitosis cell analysis, comprising:
analyzing using a computing device luminance values from a plurality of pixels in a digital image of a biological tissue sample to which Haematoxylin and Eosin stain has been applied and adjusting the luminance values if necessary, to identify a plurality of cells;
segmenting the identified plurality of cells using morphological parameters to remove non-mitotic cells;
identifying a plurality of mitotic cells from the segmented plurality of cells; and
classifying the identified plurality of mitotic cells with a pre-determined classification scheme to create a medical diagnosis or prognosis;
wherein the identifying step includes identifying plurality of mitotic cells from the segmented plurality of cells by applying one or more filters, wherein the one or more filters include a convex hull based filter, wherein applying the convex hull based filter includes: centering a plurality of neighborhood masks around a plurality of pixels on a boundary of a cell from the segmented plurality of cells; and
determining whether the plurality of pixels on the boundary of the cell belong to a convex hull of the cell, and if so, calculating a convex hull factor for the cell, and determining if the cell object is a mitotic cell using the calculated convex hull factor.

* * * * *